United States Patent [19]
Masuda et al.

[11] Patent Number: 5,986,080
[45] Date of Patent: Nov. 16, 1999

[54] CLONED NUCLEOTIDE PYROPHOSPHOHYDROLASE AND USES THEREOF

[75] Inventors: Ikuko Masuda, Wauwatosa; Joseph T. Barbieri, New Berlin; Arthur L. Haas, Brookfield; Brian D. Halligan, Wauwatosa; Daniel J. McCarty, Hartland; Lawrence M. Ryan, Wauwatosa, all of Wis.

[73] Assignee: MCW Research Foundation, Milwaukee, Wis.

[21] Appl. No.: 08/954,333

[22] Filed: Oct. 17, 1997

Related U.S. Application Data

[60] Provisional application No. 60/028,702, Oct. 18, 1996.

[51] Int. Cl.[6] .............................. C07N 21/04; C12N 9/14; C12N 1/20; C12N 15/00
[52] U.S. Cl. ..................... 536/23.2; 435/195; 435/252.3; 435/320.1; 530/350
[58] Field of Search ................................. 435/195, 252.3, 435/320.1, 4, 18, 69.1; 536/23.2; 530/350

[56] References Cited

PUBLICATIONS

A.K. Rosenthal, et al., "A comparison of the effect of transforming growth factor β1 on pyrophosphate elaboration from various articular tissues", *Arth. Rheum.* 36(4):539–542, 1993.

L.M. Ryan and D.J. McCarty, "Calcium pyrophosphate crystal deposition disease; pseudogout; articular chondrocalcinosis", *Metabolic Bone and Joint Diseases* 108:1835–1855.

L.M. Ryan and D.J. McCarty, "Calcium pyrophosphate crystal deposition disease, pseudogout, articular chondrocalcinosis", *Metabolic Bone and Joint Diseases* 111:2103–2125.

L.M. Ryan, et al., "Cartilage nucleoside triphosphate (NTP) pyrophosphohydrolase", *Arth. Rheum.* 27(4):404–409, 1984.

L.M. Ryan, et al., "Synovial Fluid ATP: A potential substrate for the production of inorganic pyrophosphate", *J. Rheum.* 18(5):716–720, 1991.

L.M. Ryan, et al., "ATP–induced chondrocalcinosis", *Arth. Rheum.* 35(12):1520–1525, 1992.

J. Sambrook, et al., "Extraction, Purification, and analysis of messenger RNA from eukaryotic cells", *Molecular Cloning. A Laboratory Manual*, 2nd ed., CSHL Press, Cold Spring Harbor, NY, pp. 7.2–7.11, 1989.

S.A. Siegel, et al., "The role of nucleoside triphosphate pyrophosphohydrolase in in vitro nucleoside triphosphate–dependent matrix vesicle calcification", *J. Biol. Chem.* 258(14):8601–8607, 1983.

J. Tenenbaum, et al., "Comparison of phosphohydrolase activities from articular cartilage in calcium pyrophosphate deposition disease and primary osteoarthritis", *Arth. Rheum.* 24(3):492–500, 1981.

P. Westfall, et al., "Articular cartilage matrix vesicles are enriched in calcium–binding phosphatidylserine compared to chondrocytes", *Crystal Arthropathy and Inflammation* poster, p. S83, 1996 (Abstract).

F. Wolfe, et al., "The American College of Rheumatology 1990 criteria for the classification of fibromyalgia", *Arth. Rheum.* 33(2):160–172, 1990.

F. Wolfe, et al., "The prevalence and characteristics of fibromyalgia in the general population", *Arth. Rheum.* 38(1):19–28, 1995.

I. Masuda, et al., "A unique ectonucleotide pyrophosphohydrolase associated with porcine chondrocyte–derived vesicles", *J. Clin. Invest.* 95:699–704, 1995.

I. Masuda, et al., "Nucleotide pyrophosphohydrolase in human synovial fluid", *J. Rheum.* 24(8):1588–1594, 1997.

I. Masuda, et al., "Ecto–nucleotide pyrophosphohydrolase (NTPPHase) in human synovial fluids (SF)", *Crystal Arthropathy and Inflammation* poster, p. S244, 1995 (Abstract).

D.J. McCarty and J.L. Hollander, "Identification of urate crystals in gouty synovial fluid", 54(3):452–460, 1961.

Z.H. Meng, et al., "Crystal–induced tumor necrosis factor (TNF) and interleukin 6 (IL6) production by a mononuclear cell line is controlled by different intracellular pathways", *Crystal Arthropathy and Inflammation* poster, p. S83, 1996 (Abstract).

A. Nishimura, et al., "The effect of anti–interleukin 8 monoclonal antibody on monosodium urate crystals–induced arthritis in rabbit", *Crystal Arthropathy and Inflammation* poster, p. S83, 1996 (Abstract).

(List continued on next page.)

*Primary Examiner*—Ponnathapura Achutamurthy
*Assistant Examiner*—Tekchand Saidha
*Attorney, Agent, or Firm*—Quarles & Brady LLP

[57] ABSTRACT

We have cloned and sequenced the cDNA encoding the 61 kD active fragment of a unique porcine chondrocyte nucleotide pyrophosphohydrolase (NTPPHase) from a porcine chondrocyte library. Degenerate oligonucleotides, corresponding to the N-terminal amino acid sequence of this peptide were hybridized to porcine chondrocyte cDNA and used to amplify DNA encoding the N-terminal sequence of 61 kD with the polymerase chain reaction (PCR). The PCR products were then used as probes to clone the entire open reading-frame for the 61 kD fragment from a porcine chondrocyte cDNA library. The length of the cloned cDNA was 2509 bp. Translation of the open-reading-frame predicts the 61 kD fragment to be a 459 amino acid protein. BLAST and FASTA analysis confirmed that this amino acid sequence was unique and did not possess high homology to any known proteins in the non-redundant protein data base. Limited homology (17%) between the 61 kD fragment and several prokaryotic and eukaryotic ATP pyrophosphate-lyase (adenylate cyclase) was detected. Northern blot analysis of porcine chondrocyte RNA showed that the DNA encoding the 61 kD fragment hybridized to a 4.3 kbp RNA transcript. Human chondrocyte RNA also hybridized to this porcine DNA probe. Coupled in vitro transcription translation of an expression vector containing the DNA insert in frame showed the expression of a 61 kD protein.

3 Claims, 9 Drawing Sheets

OTHER PUBLICATIONS

W. Ono, et al., "Characterization of a porcine chondrocyte membrane–associated nucleotide pyrophosphohydrolase (NTPPHase)", *Crystal Arthropathy and Inflammation* poster, p. S244, 1995 (Abstract).

W. Park, et al., "Inorganic pyrophosphate generation from adenosine triphosphate by cell–free human synovial fluid", *J. Rheum.* 23(4):665–671, 1996.

W. Park, et al., "Generation of inorganic pyrophosphate from extracellular adenosine triphosphate by Human Serum and Plasma", *J. Rheum.* 23(7):1233–1236, 1996.

J.W. Rachow and L.M. Ryan, "Adenosine triphosphate pyrophosphohydrolase and neutral inorganic pyrophosphatase in pathologic joint fluids", *Arth. Rheum.* 28(11):1283–1288, 1985.

J.W. Rachow, et al., "Synovial fluid inorganic pyrophosphate concentration and nucleotide pyrophosphohydrolase activity in basic calcium phosphate deposition arthropathy and Milwaukee Shoulder Syndrome", *Arth. Rheum.* 31(3):408–413, 1988.

N.F. Rebbe, et al., "Identification of nucleotide pyrophosphatase/alkaline phosphodiesterase I activity associated with the mouse plasma cell differentiation antigen PC–1", *Proc. Natl. Acad. Sci. USA* 88:5192–5196, 1991.

S.I. Belli and J.W. Goding, "Biochemical characterization of human PC–1, an enzyme possessing alkaline phosphodiesterase I and nucleotide pyrophosphatase activities", *Eur. J. Biochm.* 226:433–443, 1994.

A. Bengtsson, et al., "Muscle biopsy in primary fibromyalgia, light–microscopical and histochemical findings", *Scand. J. Rheum.* 15:1–6, 1986.

A. Bengtsson, et al., "Reduced high–energy phosphate levels in the painful muscles of patients with primary fibromyalgia", *Arth. Rheum.* 29(7):817–821, 1986.

A. Cardenal, et al., "Specificity of a porcine 127–kd nucleotide pyrophosphohydrolase for articular tissues", *Arth. Rheum.* 39(2):245–251, 1996.

A. Cardenal, et al., "Identification of a nucleotide pyrophosphohydrolase from articular tissues in human serum", *Arth. Rheum.* 39(2):252–256, 1996.

A. Cardenal, et al., "Serum nucleoside triphosphate pyrophosphohydrolase (NTPPHase) activity: Elevated levels in osteoarthritis, calcium pyrophosphate crystal deposition disease and fibromyalgia", *Crystal Arthropathy and Inflammation* poster, p. S83, 1996 (Abstract).

A. Cardenal, et al., "Characterization of nucleotide pyrophosphohydrolase (NTPPHase) in human serum", *Crystal Arthropathy and Inflammation* poster, p. S245, 1995 (Abstract).

A.M. Caswell and R.G.G. Russell, "Identification of ecto–nucleoside triphosphate pyrophosphatase in human articular chondrocytes in monolayer culture", *Bioch. Biophy. Acta* 847:40–47, 1985.

A.M. Caswell, et al., "Nucleoside triphosphate pyrophosphatase of rabbit matrix vesicles, a mechanism for the generation of inorganic pyrophosphate in epiphyseal cartilage", *Biochem. Biophy. Acta* 924:276–283, 1987.

B.A. Derfus, et al., "Articular cartilage vesicles generate calcium pyrophosphate dihydrate–like crystals in vitro", *Arth. Rheum.* 35(2):231–240, 1992.

A.P. Feinberg and B. Vogelstein, "A technique for radiolabeling DNA restriction endonuclease fragments to high specific activity", *Anal. Biochem.* 132:6–13, 1983.

A.R. Harahap and J.W. Goding, "Distribution of the murine plasma cell antigen PC–1 in non–lymphoid tissues", *J. Immun.* 141(7):2317–2320, 1988.

M. Hayashi, et al., "Differential localization of mRNAs of collagen types I and II in chick fibroblasts, chondrocytes, and corneal cells by in situ hybridization using cDNA probes", *J. Cell. Biol.* 102:2302–2309, 1986.

R. Huang, et al., "Expression of the murine plasma cell nucleotide pyrophosphohydrolase PC–1 is shared by human liver, bone, and cartilage cells", *J. Clin. Inv.* 94:560–567, 1994.

K. Ishikawa, et al., "A histological study of calcium pyrophosphate dihydrate crystal–depostion disease", *J. Bone & Joint Surg.* 71–A(6):875–886, 1989.

K. Iyama, et al., "Spatiotemporal pattern of type X collagen gene expression and collagen deposition in embryonic chick vertebrae undergoing endochondral ossification", *Anat. Rec.* 229:462–472, 1991.

E. Märker–Hermann, et al., "Proinflammatory cytokine (IL–1β, IL–6, TNF–α) production by monosodium urate crystal stimulated monocytes: Why is gout a rare disease in hyperuricemic patients with endstage renal disease?" *Crystal Arthropathy and Inflammation* poster, p. S83, 1996.

I. Masuda, et al., "A histologic and immunohistochemical study of calcium pyrophosphate dihydrate crystal deposition disease", *Clin. Ortho.* 263:272–287, 1991.

Suggs et al. PNAS, USA.,78(11):6613–6617, 1981.

Edman et al. Europ. J. Biochem., vol. 1, pp. 80–91, 1967.

2

```
                           SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

GATCGCGAAT TCGAGGACMG SACNTTCCTS GT                                          32

(2) INFORMATION FOR SEQ ID NO:2:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

RTTGGASCTC CASGGNCGTT CGAAAGCTAG                                             30

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:3:

GTSGGNAAYA TGGARATYMG                                              20

(2) INFORMATION FOR SEQ ID NO:4:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

ACGTACCCAT GGAACATATG GAGGACAGGA CTTTCC                             36

(2) INFORMATION FOR SEQ ID NO:5:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

GATCGAGAAT TCGGATCCGG TGGTGCCTCC TCAC                               34

(2) INFORMATION FOR SEQ ID NO:6:

(i) SEQUENCE CHARACTERISTICS:
            (A) LENGTH: 2509 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:6:

CAACATTATC CCCTTGGGGA TATGGATGGT GAAGACCCCA TGGGGAGCT  GGAGATCCCG    60

TCCAAGAGTT TCTACAGGCA GAATGGGAG  CCCTACACAG GAAAAGTAAA GGCCAGTGTG   120

ACCTTCCTCG ATCCCCGGAA TATTTCCACA GCCACTGCGG CCCAGAGTGA CCTGAATTTC   180

ATCAATGATG AGGGAGACAC CTTCCCCCTT CGGACATATG GCATGTTCTC TGTGGATTTC   240

ACAGATGAGG CTGCCTCAGA GTCCCTCAAT GTTGGCAAGG TGAAGGTCCA CCTCGACTCG   300

ACCCAGGTCA AGATGCCAGA GCACGTGCCC ATGATGAAAC TCTGGTCACT CAACCCAGAC   360

ACAGGGCTGT GGGAGGAGGA AGGCGACTTC CGATTTGAGA GCCAAAGGCG GAAGAGAAGA   420

GAGGACAGGA CTTTCCTGGT GGGCAACATG GAGATCCGAG AGAGGAGGCT CTTTAACCTA   480

GATGTCCCTG AAAGCAGGAG GTGCTTCATC AAGGTGAGGG CCTATCGGAG CGAGAGGTTC   540

TTGCCCAGTG AGCAGATCCA GGGGGTCGTG GTCTCTGTGA TCAACCTGGA GCCCAGGGCT   600

GGCTTTTCCT CCAACCCCAG GGCCTGGGGC CGCTTTGACA GTGTCCTCAC CGGCCCCAAT   660

GGGGCCTGTC TGCCTGCCTT CTGTGATGAC CAGTCCCCGG ATGCTTACTC CGCCTACGTT   720

CTGGCCAGCC TGGCTGGGGA AGAACTGGAA GCCGTGGAGT CTTCTCCTAA ATTCAACCCA   780

AATGCAATTG GCGTCCCTCA GCCCTACCTC AACAAGCTCA AGTACCGTCG ACAGACCAT    840

GAGGACCCAC GGGTCAAGAA GACGGCTTTC CAGATCAGCA TGGCCAAGCC AAGGCCCAAC   900

```
TCAGCTGAAG AGAGCAATGG GCCCATCTAT GCCTTTGAGA ACCTCCAGGC CTGTGAGGAG    960

GCACCACCCA GTGCAGCCCA CTTCCGGTTC TACCAGATCG AGGGGGATCG GTATGACTAC   1020

AACACGGTCC CTTTCAACGA GGATGACCCC ATGAGCTGGA CTGAAGACTA CCTGGCATGG   1080

TGGCCCAAGC CAATGGAGTT CAGGGCATGC TACATCAAGG TGAAGATCGT GGGGCCACTG   1140

GAGGTGAATG TGCGATCCCG CAACATGGGG GGCACCCACC GGCAGACAGT GGGGAAACTG   1200

TATGGAATCC GGGATGTGAA GAGCACACGG GACAGGGATC AGCCCAATGT CTCATCTGCC   1260

TGTTTGGAGT TCAAGTGCAG TGGGATGCTG TATGACCAGG ACCGTGTGGA CCGTACACTG   1320

GTAAAGGTCA TTCCCCAGGG CAGCTGCCAT CGAGCCAGCG TAAACTCCAT GCTGCACGAG   1380

TACCTGGTCA ACCACCTACC ACTAGCTGTC AATAACGACA CCAGTGAGTA CACCATGCTG   1440

GCACCCCTGG ACCCCCTGGG CCATAACTAT GGCATCTACA CTGTAACTGA CCAGGACCCT   1500

CGCACAGCCA AGGAGATTGC ACTGGGCCGA TGCTTTGATG GCAGCTCGGA TGGCTCCTCC   1560

AGAGTCATGA AGAGCAATGT GGGAGTGGCC CTCACCTTTA ACTGCGTAGA GAGGCAGGTG   1620

GGCCGTCAGA GTGCCTTCCA GTACCTCCAA AGCACCTCGG CCCGGCCCTC CCCGGCAAGC   1680

ACTGTCAGGG GAAGAGCGCC CTCCAGGAGG CAGCGGGCAA GCAGTGGTAG CCAGCGCCAG   1740

CCTAGGGGGG TGGCCTCTCT GAGGTTTCCT GGGGTTGCTC AGCAGCCTCT GAGCAACTAA   1800

GGCTTACGGT ACTTCTCTCC TTCCCCCACC TCCCGTGACA GCCATTGTGA GACTGACGCC   1860

CAAACTGTCA CTTGGTTAAT TTAAGCCCAT CTGTTCTGGT GTAACTTGCT TGTTTGTTTC   1920

TTCATGCCTT AACTTACTGT CTTTGTCCCG TGATACTGAT TGGCACGTAG CTCACAAAAT   1980

GTCAAAATAA AGCCCCTTTG TCCTCTTTAC AAGAAACACA AGAAATTGGC CATGGGCAAA   2040

CTCTGGCTTG GAGTGTTCTT CATTTAGTGC CGTCCAAGGA AATGTCCTTC CTTTTCTTTT   2100

TTTGCATGGT TTTGTCCACC TCTACAATAA TAATCTGATG TTGAAGATCA AATAACCAAT   2160

ATAAAGCGTA TTTCTTGACC TTGCTCCATA GGTTGTAAGC AAAGCCTCCA TCACAGTTCA   2220

TACAAATAAA AGGTGGTAAA ATAAAGGAAT AAACTCTAAT ATTTCTACTT GAAATGTAAA   2280

TAACATTTTC TTTGCTCAGT CTGGAGCTCT AGTGCACATT CAGTGTTACA CTGCTGAATA   2340

TAGGGTACTT GACCAAGTTT GGAAAAAACA CCTCCTGGTA TCCACAACCG GACTGGGTTG   2400

CTACTTATAT TAGCCTTTTT CCTTTTATAT TTGCTTTTGT TCTTGCTAGA AGCCTAGTGT   2460

GGCCCAGAAC AAATGTCAAT AAATGCACAT TTTATACCTG AAAAAAAAA              2509

(2) INFORMATION FOR SEQ ID NO:7:

(i) SEQUENCE CHARACTERISTICS:
        (A) LENGTH: 599 amino acids
        (B) TYPE: amino acid
        (C) STRANDEDNESS: double
        (D) TOPOLOGY: linear (ii) MOLECULE TYPE: peptide (xi) SEQUENCE DESCRIPTION: SEQ ID NO:7:

Gln His Tyr Pro Leu Gly Asp Met Asp Gly Glu Asp Pro Met Gly Glu
1               5                   10                  15

Leu Glu Ile Pro Ser Lys Ser Phe Tyr Arg Gln Asn Gly Glu Pro Tyr
            20                  25                  30

Thr Gly Lys Val Lys Ala Ser Val Thr Phe Leu Asp Pro Arg Asn Ile
        35                  40                  45

Ser Thr Ala Thr Ala Ala Gln Ser Asp Leu Asn Phe Ile Asn Asp Glu
    50                  55                  60
```

-continued

```
Gly Asp Thr Phe Pro Leu Arg Thr Tyr Gly Met Phe Ser Val Asp Phe
 65                  70                  75                  80

Thr Asp Glu Ala Ala Ser Glu Ser Leu Asn Val Gly Lys Val Lys Val
                 85                  90                  95

His Leu Asp Ser Thr Gln Val Lys Met Pro Glu His Val Pro Met Met
            100                 105                 110

Lys Leu Trp Ser Leu Asn Pro Asp Thr Gly Leu Trp Glu Glu Glu Gly
        115                 120                 125

Asp Phe Arg Phe Glu Ser Gln Arg Arg Lys Arg Arg Glu Asp Arg Thr
    130                 135                 140

Phe Leu Val Gly Asn Met Glu Ile Arg Glu Arg Arg Leu Phe Asn Leu
145                 150                 155                 160

Asp Val Pro Glu Ser Arg Arg Cys Phe Ile Lys Val Arg Ala Tyr Arg
                165                 170                 175

Ser Glu Arg Phe Leu Pro Ser Glu Gln Ile Gln Gly Val Val Val Ser
            180                 185                 190

Val Ile Asn Leu Glu Pro Arg Ala Gly Phe Ser Ser Asn Pro Arg Ala
        195                 200                 205

Trp Gly Arg Phe Asp Ser Val Leu Thr Gly Pro Asn Gly Ala Cys Leu
    210                 215                 220

Pro Ala Phe Cys Asp Asp Gln Ser Pro Asp Ala Tyr Ser Ala Tyr Val
225                 230                 235                 240

Leu Ala Ser Leu Ala Gly Glu Glu Leu Glu Ala Val Glu Ser Ser Pro
                245                 250                 255

Lys Phe Asn Pro Asn Ala Ile Gly Val Pro Gln Pro Tyr Leu Asn Lys
            260                 265                 270

Leu Lys Tyr Arg Arg Thr Asp His Glu Asp Pro Arg Val Lys Lys Thr
    275                 280                 285

Ala Phe Gln Ile Ser Met Ala Lys Pro Arg Pro Asn Ser Ala Glu Glu
290                 295                 300

Ser Asn Gly Pro Ile Tyr Ala Phe Glu Asn Leu Gln Ala Cys Glu Glu
305                 310                 315                 320

Ala Pro Pro Ser Ala Ala His Phe Arg Phe Tyr Gln Ile Glu Gly Asp
                325                 330                 335

Arg Tyr Asp Tyr Asn Thr Val Pro Phe Asn Glu Asp Asp Pro Met Ser
            340                 345                 350

Trp Thr Glu Asp Tyr Leu Ala Trp Trp Pro Lys Pro Met Glu Phe Arg
        355                 360                 365

Ala Cys Tyr Ile Lys Val Lys Ile Val Gly Pro Leu Glu Val Asn Val
    370                 375                 380

Arg Ser Arg Asn Met Gly Gly Thr His Arg Gln Thr Val Gly Lys Leu
385                 390                 395                 400

Tyr Gly Ile Arg Asp Val Lys Ser Thr Arg Asp Arg Asp Gln Pro Asn
                405                 410                 415

Val Ser Ser Ala Cys Leu Glu Phe Lys Cys Ser Gly Met Leu Tyr Asp
            420                 425                 430

Gln Asp Arg Val Asp Arg Thr Leu Val Lys Val Ile Pro Gln Gly Ser
        435                 440                 445

Cys His Arg Ala Ser Val Asn Ser Met Leu His Glu Tyr Leu Val Asn
    450                 455                 460

His Leu Pro Leu Ala Val Asn Asn Asp Thr Ser Glu Tyr Thr Met Leu
465                 470                 475                 480

Ala Pro Leu Asp Pro Leu Gly His Asn Tyr Gly Ile Tyr Thr Val Thr
                485                 490                 495
```

```
Asp Gln Asp Pro Arg Thr Ala Lys Glu Ile Ala Leu Gly Arg Cys Phe
            500                 505                 510

Asp Gly Ser Ser Asp Gly Ser Ser Arg Val Met Lys Ser Asn Val Gly
        515                 520                 525

Val Ala Leu Thr Phe Asn Cys Val Glu Arg Gln Val Gly Arg Gln Ser
    530                 535                 540

Ala Phe Gln Tyr Leu Gln Ser Thr Ser Ala Arg Pro Ser Pro Ala Ser
545                 550                 555                 560

Thr Val Arg Gly Arg Ala Pro Ser Arg Arg Gln Arg Ala Ser Ser Gly
                565                 570                 575

Ser Gln Arg Gln Pro Arg Gly Val Ala Ser Leu Arg Phe Pro Gly Val
                580                 585                 590

Ala Gln Gln Pro Leu Ser Asn
                595
```

(2) INFORMATION FOR SEQ ID NO:8:

(i) SEQUENCE CHARACTERISTICS:
        (A) LENGTH: 2797 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

```
GGAGTATCGT GCGGGGCCGG TGTCAGCGCC GCTGACAATG GGAACCCAT GCGCTTTGGC      60

CACGTGTATC TGGGGAACAA TCGTGTGAGC ATGACTGGCT ACAAAGGCAC GTTCACCCTC    120

CACGTGCCCC AGGACACGGA GAGGCTGGTG CTTACATTTG TGGACAGGCT GCAGAAGTTT    180

GTCAACACCA CCAAAGTGCT GCCCTTTAAC AAGAAGGGAA GTGCAGTGTT CCATGAGATC    240

AAGAATGCTT CGGCGGAAAG AACCCATCAT CTTGGAGGCC ATGGAGACCA ACATTATCCC    300

CTTGGGGATA TGGATGGTGA AGACCCCATG GGGGAGCTGG AGATCCCGTC CAAGAGTTTC    360

TACAGGCAGA ATGGGGAGCC CTACACAGGA AAAGTAAAGG CCAGTGTGAC CTTCCTCGAT    420

CCCCGGAATA TTTCCACAGC CACTGCGGCC CAGAGTGACC TGAATTTCAT CAATGATGAG    480

GGAGACACCT TCCCCCTTCG GACATATGGC ATGTTCTCTG TGGATTTCAC AGATGAGGCT    540

GCCTCAGAGC CCCTCAATGT TGGCAAGGTG AAGGTCCACC TCGACTCGAC CCAGGTCAAG    600

ATGCCAGAGC ACGTGCCCAT GATGAAACTC TGGTCACTCA ACCCAGACAC AGGGCTGTGG    660

GAGGAGGAAG GCGACTTCCG ATTTGAGAGC CAAAGGCGGA AGAGAAGAGA GGACAGGACT    720

TTCCTGGTGG GCAACATGGA GATCCGAGAG AGGAGGCTCT TTAACCTAGA GTCCCTGAA    780

AGCAGGAGGT GCTTCATCAA GGTGAGGGCC TATCGGAGCG AGAGGTTCTT GCCCAGTGAG    840

CAGATCCAGG GGGTCGTGGT CTCTGTGATC AACCTGGAGC CAGGGCTGG CTTTTCCTCC     900

AACCCCAGGG CCTGGGGCCG CTTTGACAGT GTCCTCACCG GCCCCAATGG GGCCTGTCTG    960

CCTGCCTTCT GTGATGACCA GTCCCCGGAT GCTTACTCCG CCTACGTTCT GGCCAGCCTG   1020

GCTGGGGAAG AACTGGAAGC CGTGGAGTCT TCTCCTAAAT TCAACCCAAA TGCAATTGGC   1080

GTCCCTCAGC CCTACCTCAA CAAGCTCAAG TACCGTCGGA CAGACCATGA GGACCCACGG   1140

GTCAAGAAGA CGGCTTTCCA GATCAGCATG GCCAAGCCAA GGCCCAACTC AGCTGAAGAG   1200

AGCAATGGGC CCATCTATGC CTTTGAGAAC CTCCAGGCCT GTGAGGAGGC ACCACCCAGT   1260

GCAGCCCACT TCCGGTTCTA CCAGATCGAG GGGGATCGGT ATGACTACAA CACGGTCCCT   1320

TTCAACGAGG ATGACCCCAT GAGCTGGACT GAAGACTACC TGGCATGGTG GCCCAAGCCA   1380
```

```
ATGGAGTTCA GGGCATGCTA CATCAAGGTG AAGATCGTGG GGCCACTGGA GGTGAATGTG    1440

CGATCCCGCA ACATGGGGGG CACCCACCGG CAGACAGTGG GGAAACTGTA TGGAATCCGG    1500

GATGTGAAGA GCACACGGGA CAGGGATCAG CCCAATGTCT CATCTGCCTG TTTGGAGTTC    1560

AAGTGCAGTG GGATGCTGTA TGACCAGGAC CGTGTGGACC GTACACTGGT AAAGGTCATT    1620

CCCCAGGGCA GCTGCCATCG AGCCAGCGTA AACTCCATGC TGCACGAGTA CCTGGTCAAC    1680

CACCTACCAC TAGCTGTCAA TAACGACACC AGTGAGTACA CCATGCTGGC ACCCCTGGAC    1740

CCCCTGGGCC ATAACTATGG CATCTACACT GTAACTGACC AGGACCCTCG CACAGCCAAG    1800

GAGATTGCAC TGGGCCGATG CTTTGATGGC AGCTCGGATG GCTCCTCCAG AGTCATGAAG    1860

AGCAATGTGG GAGTGGCCCT CACCTTTAAC TGCGTAGAGA GGCAGGTGGG CCGTCAGAGT    1920

GCCTTCCAGT ACCTCCAAAG CACCTCGGCC CGGCCCTCCC CGGCAAGCAC TGTCAGGGGA    1980

AGAGCGCCCT CCAGGAGGCA GCGGGCAAGC AGTGGTAGCC AGCGCCAGCC TAGGGGGGTG    2040

GCCTCTCTGA GGTTTCCTGG GGTTGCTCAG CAGCCTCTGA GCAACTAAGG CTTACGGTAC    2100

TTCTCTCCTT CCCCCACCTC CCGTGACAGC CATTGTGAGA CTGACGCCCA AACTGTCACT    2160

TGGTTAATTT AAGCCCATCT GTTCTGGTGT AACTTGCTTG TTTGTTTCTT CATGCCTTAA    2220

CTTACTGTCT TTGTCCCGTG ATACTGATTG GCACGTAGCT CACAAAATGT CAAAATAAAG    2280

CCCCTTTGTC CTCTTTACAA GAAACACAAG AAATTGGCCA TGGGCAAACT CTGGCTTGGA    2340

GTGTTCTTCA TTTAGTGCCG TCCAAGGAAA TGTCCTTCCT TTTCTTTTTT TGCATGGTTT    2400

TGTCCACCTC TACAATAATA ATCTGATGTT GAAGATCAAA TAACCAATAT AAAGCGTATT    2460

TCTTGACCTT GCTCCATAGG TTGTAAGCAA AGCCTCCATC ACAGTTCATA CAAATAAAAG    2520

GTGGTAAAAT AAAGGAATAA ACTCTAATAT TTCTACTTGA AATGTAAATA ACATTTTCTT    2580

TGCTCAGTCT GGAGCTCTAG TGCACATTCA GTGTTACACT GCTGAATATA GGGTACTTGA    2640

CCAAGTTTGG AAAAACACC TCCTGGTATC CACAACCGGA CTGGGTTGCT ACTTATATTA    2700

GCCTTTTTCC TTTTATATTT GCTTTTGTTC TTGCTAGAAG CCTAGTGTGG CCCAGAACAA    2760

ATGTCAATAA ATGCACATTT TATACCTGAA AAAAAAA                              2797
```

(2) INFORMATION FOR SEQ ID NO:9:

(i) SEQUENCE CHARACTERISTICS:
        (A) LENGTH: 1716 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

```
AGCACATATC CACAGTGAAA CTCTGGTCAC TCAATCCAGA CACAGGGCTG TGGGAGGAGG      60

AAGGTGATTT CAAATTTGAA AATCAAAGGA GGAACAAAAG AGAAGACAGA ACCTTCCTGG     120

TGGGCAACCT GGAGATTCGT GAGAGGAGGC TCTTTAACCT GGATGTTCCT GAAAGCAGGC     180

GGTGCTTTGT TAAGGTGAGG GCCTACCGGA GTGAGAGGTT CTTGCCTAGT GAGCAGATCC     240

AGGGGGTTGT GATCTCCGTG ATTAACCTGG AGCCTAGAAC TGGCTTCTTG TCCAACCCTA     300

GGGCCTGGGG CCGCTTTGAC AGTGTCATTC ACAGCCCCAA CGGGGCCTGT GTGCCTGCCT     360

TCTGTGATGA CCAGTCCCCT GATGCCTACT CTGCCTATGT CTTGGMAAGC CTGGCTGGGG     420

AGGAACTGCA AGCAGTGGAG TCTTCTCCTA AATTCAACCC AAATGCAATT GGCGTCCCTC     480

AGCCCTATCT CAACAAGCTC AACTACCGTC GGACGGACCA TGAGGATCCA CGGGTTAAAA     540
```

```
AGACAGCTTT CCAGATTAGC ATGGCCAAGC CAAGGCCCAA CTCAGCTGAG GAGAGCAATG      600

GGCCCATCTA TGCCTTTGAG AACCTCCGGG CATGTGAAGA GGCACCACCC AGTGCAGCCC      660

ACTTCCGGTT CTACCAGATT GAGGGGGATC GATATGACTA CAACACAGTC CCCTTCAACG      720

AAGATGACCC TATGAGCTGG ACTGAAGACT ATCTGGCATG GTGGCCAAAG CCGATGGAAT      780

TCAGGGCCTG CTATATCAAG GTGAAGATTG TGGGGCCACT GGAAGTGAAT GTGCGATCCC      840

GCAACATGGG GGGCACTCAT CGGCGGACAG TGGGGAAGCT GTATGGAATC CGAGATGTGA      900

GGAGCACTCG GGACAGGGAC CAGCCCAATG TCTCAGCTGC CTGTCTGGAG TTCAAGTGCA      960

GTGGGATGCT CTATGATCAG GACCGTGTGG ACCGCACCCT GGTGAAGGTC ATCCCCCAGG     1020

GCAGCTGCCG TTGAGCCAGT GTGAACCCCA TGCTGCATGA GTACCTGGTC AACCACTTGC     1080

CACTTGCAGT CAACAACGAC ACCAGTGAGT ACACCATGCT GGCACCCTTG GACCCACTGG     1140

GCCACAACTA TGGCATCTAC ACTGTCACTG ACCAGGACCC TCGCACGGCC AAGGAGATCG     1200

CGCTCGGCCG GTGCTTTGAT GGCACATCCG ATGGCTCCTC CAGAATCATG AAGAGCAATG     1260

TGGGAGTAGC CCTCACCTTC AACTGTGTAG AGAGGCAAGT AGGCCGCCAG AGTGCCTTCC     1320

AGTACCTCCA AAGCACCCCA GCCCAGTCCC CTGCTGCAGG CACTGTCCAA GGAAGAGTGC     1380

CCTCGAGGAG GCAGCAGCGA GCGAGCAGGG GTGGCCAGCG CCAGAGTGGA GTGGTGGCCT     1440

CTCTGAGATT TCCTAGAGTT GCTCAACAGC CCCTGATCAA CTAAGTTTTG TGGTACTTCA     1500

CCCTCTTCTG CCCTCATTTC ATGTGACAGC CATTGTGAGA CTGATGCACA AACTGTCACT     1560

TGGTTAATTT AAGCACTTCT GTTTTCGTGA ATTTGCTTGT TTGTTTCTTC ATGCCTTTAC     1620

TTACTTTGTC CCATGCTACT GATTGGCACG TGGCCCCCAC AATGGCACAA TAAAGCCCCT     1680

TTGTGAAAAA AAAAAAAAA AAAAAAAAAA AAAAAA                                1716
```

CLONED NUCLEOTIDE PYROPHOSPHOHYDROLASE AND USES THEREOF

CROSS-REFERENCE TO RELATED APPLICATIONS

This application claims the benefit of U.S. Provisional application No. 60/028,702, filed Oct. 18, 1996.

BACKGROUND OF THE INVENTION

1. Field of the Invention

The present invention relates generally to the manipulation of genetic materials and particularly to the manufacture and use of specific DNA sequences useful in recombinant procedures to secure the production of peptides having one or more properties of nucleotide pyrophosphohydrolase.

2. Background of the Art

Calcium pyrophosphate dihydrate (CPPD) crystal deposition in human articular cartilage is a common age-dependent event often associated with degeneration of articular tissues and/or with acute attacks of arthritis (D. McCarty, et al., 56 *Ann. Intern. Med.* 711–737 (1962)). Prospects for preventing or reversing CPPD crystal deposition depends on a better understanding of inorganic pyrophosphate ($PP_i$) metabolism in joint tissues. Synovial fluid $PP_i$ levels are nearly always greater than those of plasma and correlate directly with the degree of radiographically evident joint degeneration (L. Ryan, et al., In Arthritis and Allied Conditions, 12th ed., D. McCarty, et al., editors, pp. 1835–1855 (1993)). $PP_i$ is released into the ambient medium when cartilage slices or isolated chondrocytes but not other joint tissues are cultured in vitro, suggesting that this tissue is the source of synovial fluid $PP_i$. Detergent extracts of CPPD crystal-encrusted degenerated cartilage contained increased nucleotide pyrophosphohydrolase (NTPPHase) activity relative to normal or degenerated cartilage without crystals (J. Tenenbaum, et al., 24 *Arthritis Rheum.* 294–300 (1981)). This enzyme generates $PP_i$ from ATP and other nucleotides. NTPPHase is an ectoenzyme in canine (L. Ryan, et al., 27 *Arthritis Rheum.* 404–409 (1984)) and in human (A. Caswell, et al., 847 *Biochem. Biophys. Acta.* 40–47 (1985)) chondrocytes. ATP levels were significantly higher in knee joint fluids containing CPPD crystals compared with fluids from osteoarthritis (217 vs. 98 nM) (L. Ryan, et al., 18 *J. Rheumatol.* 716–720 (1991)) despite higher activity of NTPPHase in the former (J. Rachow, et al., 28 *Arthritis Rheum.* 1283–1288 (1985)).

EctoNTPPHase activity is also associated with vesicles derived from chondrocytes in epiphyseal cartilage, termed matrix vesicles, and is thought by some investigators important for in vitro calcification (S. Siegal, et al., 258 *J. Biol. Chem.* 8601–8607 (1983); A. Caswell, et al., 924 *Biochem. Biophys. Acta.* 276–283 (1987)). Addition of ATP to vesicles isolated from adult porcine (B. Derfus, et al., 35 *Arthritis Rheum.* 231–240 (1992)) or human (L. Ryan, et al., 35 *Arthritis Rheum.* 1520–1525 (1992)) hyaline articular cartilage, termed articular cartilage vesicles (ACV), formed a mineral phase tentatively identified as monoclinic CPPD.

The inventors have noted an enzyme activity on the exterior of many cells which generates inorganic pyrophosphate ($PP_i$), a necessary constituent of pathologic crystals which form in cartilages of patients with a specific form of arthritis termed calcium pyrophosphate dihydrate (CPPD) crystal deposition disease. The enzyme is called nucleotide pyrophosphohydrolase (NTPPH) because of one reaction which it catalyzes, the hydrolysis of nucleoside triphosphates such as ATP to a nucleoside monophosphate and $PP_i$. This enzyme activity is very likely an important if not essential factor in the generation of $PP_i$ which then forms CPPD crystals.

There are many forms of NTPPH. One specific form has been characterized in our laboratory and is termed 127 kD NTPPH, based upon its molecular weight. Antibodies raised against porcine (pig) 127 kD NTPPH have been used to determine the tissue distribution, and 127 kD NTPPH was found only in tissues in or around joints. Within these articular tissues, 127 kD is most concentrated in cartilage. In chondrocytes, the cells of cartilage, 127 kD NTPPH is restricted to vesicles termed articular cartilage vesicles (ACV). These are important structures which can mineralize to form CPPD crystals when a substrate such as ATP is added. These are the only structures that have ever been found to serve as a nidus for CPPD formation and they are very enriched in the 127 kD enzyme.

The native 127 kD enzyme is attached to the membranes of these vesicles. However, antibody to 127 kD NTPPH also identifies putative breakdown fragments that are of lower molecular weight, that are soluble, and that still possess enzyme activity. These have been identified in the joint fluid surrounding cartilage and in the serum of humans, but not in tissues. In joint fluid and serum the activity of this enzyme has been found to be elevated in patients who have CPPD crystals in their cartilage and to a lesser degree in patients who have osteoarthritis.

It would be advantageous to clone cDNA encoding nucleotide pyrophosphohydrolase so that sufficient quantities of NTPPH can be generated for use in further studies and diagnostic testing.

BRIEF SUMMARY OF THE INVENTION

One aspect of the invention provides a DNA construct encoding a soluble portion of nucleotide pyrophosphohydrolase (NTPPH), wherein the NTPPH can be porcine NTPPH.

A further aspect provides a DNA construct wherein the construct comprises a coding sequence according to that of SEQ ID NO:6.

Another aspect provides a soluble portion of isolated nucleotide pyrophosphohydrolase (NTPPH). The NTPPH can be porcine.

A still further aspect of the invention provides a soluble portion of isolated NTPPH, wherein the NTPPH comprises a coding sequence according to that of SEQ ID NO:7.

Yet another aspect of the invention provides an isolated RNA construct encoding for nucleotide pyrophosphohydrolase that can hybridize with a DNA construct having a coding sequence according to that of SEQ ID NO:6 when the RNA construct and the DNA construct are subjected to Northern blot analysis. The RNA can be isolated human RNA.

Another aspect of the invention provides a nucleotide pyrophosphohydrolase enzyme expressed when a competent host organism is transformed with the above DNA constructs. Preferably, the enzyme is of a purity and/or quantity greater than that available natively.

Yet another aspect provides a method of determining the efficacy of a pharmacologic agent for inhibiting the enzymatic activity of nucleotide pyrophosphohydrolase, comprising the steps of: measuring the enzymatic activity of a nucleotide pyrophosphohydrolase of the above kind; mixing the nucleotide pyrophosphohydrolase with the pharmacologic agent; and measuring the enzymatic activity of the mixture.

Another aspect provides an antibody raised in response to a nucleotide pyrophosphohydrolase of the above kind.

A still further aspect provides a method of determining the presence of nucleotide pyrophosphohydrolase in biological fluids, comprising the steps of: mixing an antibody of the above kind with the biological fluid; screening the mixture by ELISA; and determining the presence or absence of nucleotide pyrophosphohydrolase. The biological fluid can be from articular tissues or serum.

Another aspect provides a method of determining the presence and location of nucleotide pyrophosphohydrolase in biological tissues, comprising the step of: detecting the presence or absence of hybridization when the biological tissue is exposed to a DNA construct of the above kind.

The utilities of the presently disclosed cDNA include:
1. Using the cDNA to generate sufficient 61 kD NTPPH containing the active site of the enzyme such that pharmacologic agents can been screened for NTPPH inhibitory activity. The specific inhibition of this enzyme would be useful toward diminishing the production of $PP_i$ which is a component of the pathologic CPPD crystals in articular cartilage.
2. The cDNA can be used to generate sufficient 61 kD NTPPH containing the active enzyme site of sufficient purity, such that crystallization of the enzyme may be accomplished allowing characterization of its tertiary structure. This information can then be used to design inhibitory drugs.
3. Using the cDNA to generate 61 kD NTPPH of sufficient purity to serve as a standard for immunologically based assays of serum and joint fluid determinations of the parent 127 kD NTPPH and its breakdown products. These determinations may be useful in predicting CPPD crystal formation. Since this enzyme is restricted to articular tissues, its detection in elevated quantities in joint fluid or blood would imply joint tissue damage.
4. Using the cDNA to generate 61 kD NTPPH of sufficient purity as to be an ideal antigen for raising an antibody with specificity for this molecule. This antibody could then be used for testing biological fluids by ELISA for content of the 61 kD NTPPH, a putative marker of joint tissue breakdown and of vesical formation within articular tissues.
5. Using the cDNA as a unique reagent for in situ hybridization studies to determine the presence and location of mRNA for the parent molecule within cartilage and other tissues.

The objects of the present invention, therefore, include providing a cDNA and methods of the above kind;

(a) which are useful in developing pharmacologic agents which can diminish the production of $PP_i$;

(b) which provide diagnostic determinations which are useful in predicting CPPD crystal formation; and (c) providing a diagnostic determination of the presence and location of mRNA for the parent NTPPH molecule within cartilage and other tissues.

These and still other objects and advantages of the present invention will apparent from the description which follows. The following description is merely of the preferred embodiments. Thus, the claims should be looked to in order to understand the full scope of the invention.

DETAILED DESCRIPTION OF THE INVENTION

INTRODUCTION

Figure 1:
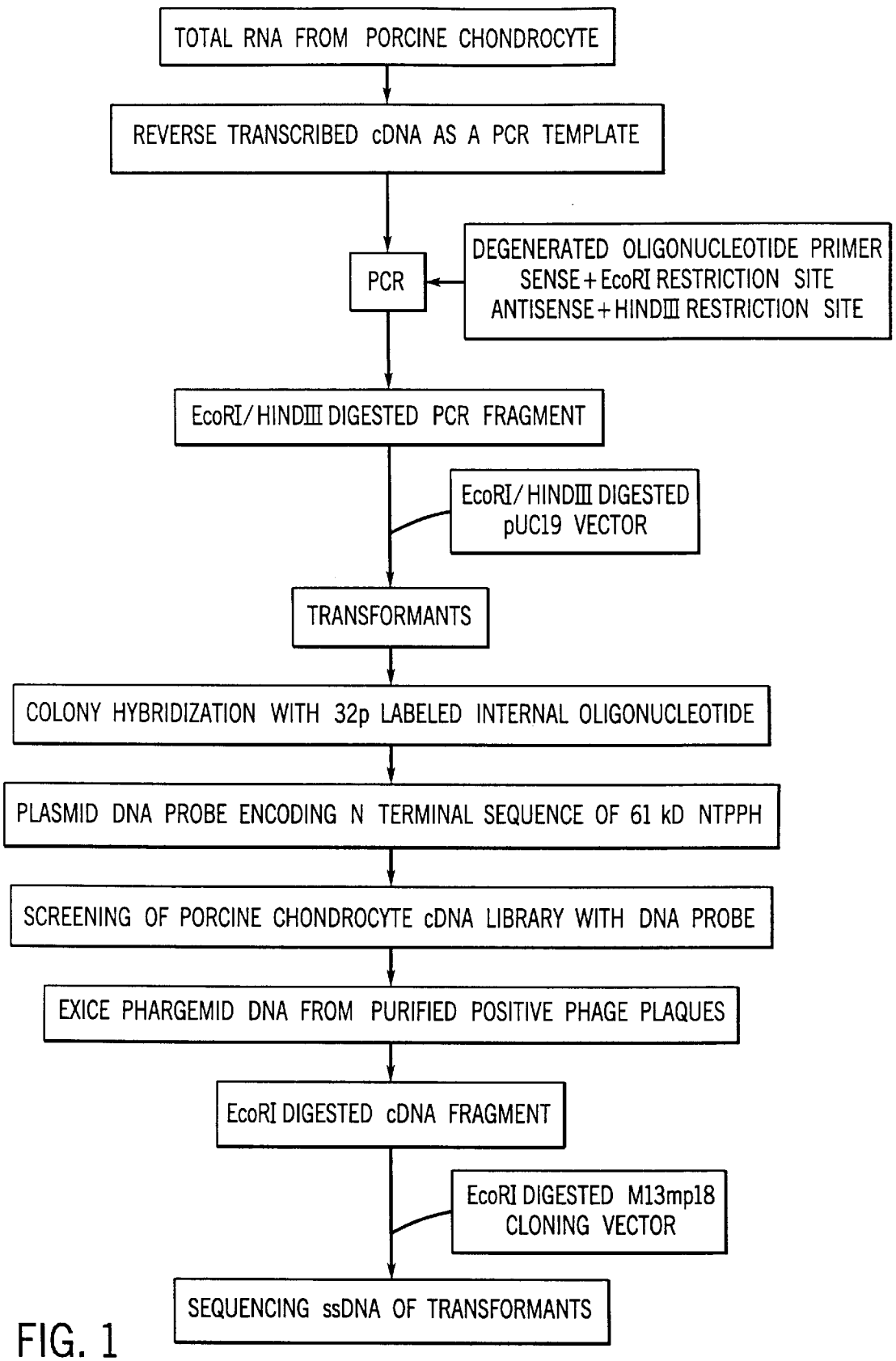
FIG. 1 shows the cloning strategy of the present invention.

Modulation of inorganic pyrophosphate ($PP_i$) metabolism in articular tissue may prevent calcium pyrophosphate dihydrate (CPPD) crystal deposition and accelerated joint tissue degradation. CPPD crystal deposition often occurs in aged or degenerative articular cartilage and sometimes cause acute arthritis ("pseudogout") (reviewed in L. Ryan and D. McCarty, In Arthritis and Allied Conditions, 12th Ed., Lea & Febiger, Malvern, Philadelphia 1835–1855 (1993)). Several studies indicated the $PP_i$ is produced from extracellular ATP by joint tissue ecto-nucleotide pyrophosphohydrolase (NTPPH) (J. Rachow, et al., 31 Arthritis Rheum. 408–413 (1988); L. Ryan, et al., 18 J. Rheumatol. 716–720 (1991); W. Park, et al., 23 J. Rheumatol. 665–671 (1996)). Mean extracellular ATP levels were higher in the knee joint fluids containing CPPD crystals compared with fluids from osteoarthritis (OA) (Ryan, et al., supra, 1991) despite higher activity of NTPPH in the former (Ryan, et al., supra, 1991; J. Ryan and L. Rachow, 28 Arthritis Rheum. 1283–1288 (1985)). $PP_i$ levels correlated positively with NTPPH activity in joint fluids (Rachow, et al., supra, 1988). ATP was converted stoichiometrically to $PP_i$ by cell-free joint fluids from OA or CPPD patients (L. Ryan, et al., supra, 1991). Detergent extracts of CPPD crystal-encrusted degenerated cartilage contained increased NTPPH activity relative to normal or degenerated cartilage without crystal (J. Tenenbaum, et al., 24 Arthritis Rheum. 294–300 (1981)). NTPPH activity in ultra-sedimentable fraction of joint fluids from patients with CPPD was more elevated than those with OA, rheumatoid arthritis, bursitis, or fluids from normal individuals (I. Masuda, et al., 38 Arthritis Rheum. 244 (1995)). In addition, cell-free fluid NTPPH activity correlated with the radiographic grade of joint degradation in OA and CPPD patients (I. Masuda, et al., supra, 1995). Despite studies which implicated the overexpression of NTPPH as the mechanism responsible for this pathological condition, the physiological, and pathological features of NTPPH have not been determined.

We have identified sedimentable (vesicle-associated) 127 kD chondrocyte NTPPH and a soluble 61 kD active split product from 127 kD NTPPH in porcine articular cartilage organ culture conditioned media (I. Masuda, et al., 95 *J. Clin. Invest.* 699–705 (1995)). Antibodies to porcine 61 kD NTPPH cross-reacted with 61 and 127 kD protein in normal and pathological human joint fluid (I. Masuda, et al., supra, 1995) and with 100 kD soluble fragment with identical kinetics with the porcine NTPPH in human sera (A. Cardenal, et al., 39 *Arthritis Rheum.* 252–256 (1996)). 127 kD NTPPH was found only in articular tissue such as hyaline cartilage, fibro cartilage, tendon, ligament (A. Cardenal, et al., 39 *Arthritis Rheum.* 245–251 (1996)), and synovial membrane (I. Masuda, et al., supra, 1995), all tissues that elabolate extracellular $PP_i$. Another protein which has nucleotide pyrophosphatase activity, known as the membrane protein plasma cell differentiation antigen, PC-1 (N. Reebe, 88 et al., *Proc. Natl. Acad. Sci. USA* 5192–5196 (1991); N. Reebe, et al., 30 *Mol. Immunol.* 87–93 (1993)), has also been expressed in many types of cells (A. Harahap and J. Goding, 141 *J. Immunol.* 2317–2320 (1988)), the 61 kD NTPPH apparent be unique to PC-1, the N-terminal amino acid sequence of the soluble, enzymatically active 61 kD had little homology to PC-1 (I. Masuda, et al., supra, 1995).

Tissue specificity and activity in human serum suggest that NTPPH may serve as a marker of articular tissue metabolism.

The present invention discloses the molecular properties of the 61 kD NTPPH.

EXPERIMENTAL PROCEDURES

1. Construction of Porcine Articular Chondrocyte cDNA Library Isolation of RNA from Porcine Articular Chondrocytes Chondrocytes were cultured at high density and maintained as primary monolayer cultures in DMEM containing 10% FBS and 1% penicillin/streptomycin/Fungisone (PSF) as described (I. Masuda, et al., supra, 1995). Total RNA was isolated from chondrocytes using a standard nonionic detergent method with 1000 u/ml of human placental RNAse inhibitor (Amersham, Arlington Heights, Ill.) (J. Sambrook, et al., Molecular Cloning. A Laboratory Manual, 2nd ed. CSHL Press, Cold Spring Harbor, N.Y. (1989)). The amount of RNA was quantitated by spectrophotometric absorbance at 260 and 280 nm. Poly(A) RNA was selected twice from total RNA using a oligo(dT) cellulose column chromatography (GibcoBRL, Gaithersburg, Md.) (J. Sambrook, et al., supra, 1989).

2. cDNA Synthesis cDNA was synthesized from 5 g Poly(A) RNA using SUPERSCRIPT-Choice System (GibcoBRL, Gaithersburg, Md.). A mix of oligo(dT) 12–18 primer and random hexamers were used to prime mRNA. EcoRI adaptor was added to both ends of synthesized cDNA fragment and then phospholyrated. cDNA smaller than 500 bp and unincorporated adaptor were removed using cDNA size fractionation column chromatography. Population and size of cDNA was examined by alkaline agarose gel electrophoresis (J. Sambrook, et al., supra, 1989).

3. Construction and characterization of cDNA library cDNA was ligated into lambda ZAP II phage EcoRI armPP$_i$ s. Packaging into phage capsule were carried out using GIGAPACK-(Stratagene, La Jolla, Calif.). Titering and cDNA insert analysis showed that the titer of this unamplified and amplified library was 1×109 and 1×1011 pfu/ml, respectively, that the average length of cDNA was 1.4 kbp.

4. Cloning of Porcine 61 kD NTPPH and Amplification of Nucleic Acid Probes encoding 61 kD NTPPHase 61 kD NTPPHase was purified from conditioned media of organ-cultured porcine articular cartilage as previously described (I. Masuda, et al., supra, 1995). Its N terminus that was sequenced through 26 cycles showed <30% homology to known protein data bases and was used as a template to design degenerative oligonucleotide primers based on common codon usage of human proteins. First, a cDNA template was synthesized from porcine chondrocyte total RNA by reverse transcriptase (Perkin-Elmer, Emeryville, Calif.). Using this cDNA as a template, DNA fragment specific for the N terminus of the 61 kD peptide was amplified with sense degenerative oligonucleotides primer which contained a EcoRI restriction site; 5'-GATCGCGAATTCGAGGACMGSACNTTCCTSGT-3', (SEQ ID NO:1) and antisense primer which contained a HindIII site; 3'-RTTGGASCTCCASGGNCGTTCGAAAGCTAG-5' (SEQ ID NO:2) (See FIG. 2).

The amplification scheme was as follows: precycle, 90 seconds incubation at 94° C.; cycles 1–5, 94° C. for 30 seconds, 35° C. for 60 seconds, and 68° C. for 60 seconds; cycles 6–35, 94° C. for 30 seconds, 45° C. for 60 seconds, and 68° C. for 60 seconds. Using the first PCR product as a template, another 30 cycle reaction (95° C. for 30 seconds, 55° C. for 60 seconds, and 68° C. for 60 seconds) was carried out. The amplified product ~100 bp, was identified by electrophoresis in a 1.8% agarose gel. The amplified DNA fragment was digested with EcoRI and HindIII, then extracted from PCR reaction mixture with glass fog (MERMAID, Bio101, Vista, Calif.). The fragment was cloned into the EcoRI and HindIII restriction site of pUC19. The plasmid were then transformed into a competent *E coli.* TG1. Transformants were selected by a-complementation as white colonies on Ap plates. Colonies were transferred to a nitrocellulose membrane. The membrane was soaked in SDS alkaline solution, neutralized, washed, and DNA was UV cross-linked. The membrane was subjected to Southern blotting using a $^{32}$P-labeled degenerative oligonucleotide 5'-GTSGGNAAYATGGARATYMG-3' (SEQ ID NO:3) (J. Sambrook, et al., supra, 1989). Plasmid DNA from positive colonies was isolated with QAEGEN column (QAEGEN Inc., Chatsworth, Calif.). Both strands of the cDNA inserts were sequenced by the dideoxy chain-termination method using fluorescein primer and AutoRead-Sequencing kit (Pharmacia Biotech, Piscataway, N.J.), and ALF-DNA Sequencer (Pharmacia Biotech, Piscataway, N.J.). DNA encoding N-terminal 61 kD NTPPH amino acid sequence was identified. This DNA was used as DNA probe to screen cDNA library.

5. Cloning DNA encoding the 61 kD NTPPH from porcine chondrocyte cDNA library

Amplified lambda ZAP II phage containing cDNA library were plated at a density of 3×104 cells per 150 mm plate. The DNA from the phage plaques was transferred to duplicate nitrocellulose membranes and UV cross-linked after denaturation and renaturation steps. The membranes were screened with the DNA probe which had been radiolabeled (A. Feinberg and B. Vogelstein, *Anal. Biochem.* 132 (1984)). Positive phage plaques were identified and subjected to 2–3 additional rounds of plating and screening. Purified positive phage were isolated from media, co-infected with helper phage into the SOLOR host cell to excise the phagemid containing the cDNA insert. DNA was digested with EcoRI, and their sizes and restriction maps were determined. One of cDNA length 2.5 kbp was subjected to sequencing. cDNA fragment were ligated, in both orientation, into the EcoRI site of the replicative forms of M13mp18 cloning phage and nucleotide sequences of its ssDNA were determined using fluorescent labeled primer and the ALF-DNA sequencer.

6. Computed database search for sequenced nucleotides

GCG program (Genetic Computer Group, Madison, Wis.) was used to map, translate, and motifs search the determined sequence of the NTPPH. Non-redundant nucleotide and protein data bases (FASTA, BLAST) were searched to examine its homology.

7. Expression of porcine chondrocyte 61 kD NTPPH RNA analysis

Total RNA from porcine chondrocyte and human osteoarthritic cartilage chondrocytes was isolated (J. Sambrook, et al., supra, 1989). Both porcine and human chondrocyte RNA (10 g) were electrophoresed in formaldehyde/agarose gels (J. Sambrook, et al., supra, 1989), vacuum transferred to MSI nylon membrane (MSI, Westboro, Mass.) which was UV cross-linked. The membrane was prehybridized for 2 hours at 42° C. in 50% formamide, 5×SSPE, 5×Denhardt's reagent, 0.1% SDS, and 100 g/ml denatured salmon sperm DNA and then hybridized overnight at 42° C. in 50% formamide, 5×SSPE, 1×Denhardt's, 0.1% SDS, 20 g/ml denatured salmon sperm DNA, with a $^{32}$P-labeled cDNA probe, containing the 2.5 kbp fragment. The probe was radiolabeled was a random-primer labeling kit (Ready-To-Go-DNA labering Beads, Phermacia, Piscataway, N.J.). After hybridization, membranes were washed (0.25×SSC, 0.1% SDS) at 65° C. subjected to autoradiography. As a control probe, chicken beta actin cDNA was hybridized to the same membrane that had been stripped of the former probe.

8. Construction of Expression vector

PCR strategy was used to introduce unique NdeI (5') and BamHI (3') restriction sites in the cDNA encoding the 61 kD NTPPH (FIG. 2) and this fragment was cloned into two expression vectors PET15b and PET22b (Novagen, Madison, Wis.). PET15b has a His tag downstream of T7 promoter, and PET22b vector has a leader sequence downstream of T7 to fold recombinant protein properly in periplasm. First, sense primer containing NcoI and NdeI site, and start N-terminal amino acid sequence in frame, was designed as 5'-ACGTACCCATGGAACATA TGGAGGACAGGACTTTCC-3' (SEQ ID NO:4) and antisense primer containing BamHI and EcoRI site as 5'-GATCGAGAATTCGGATCC GGTGGTGCCTCCTCAC-3' (SEQ ID NO:5), were designed.

Figure 3:
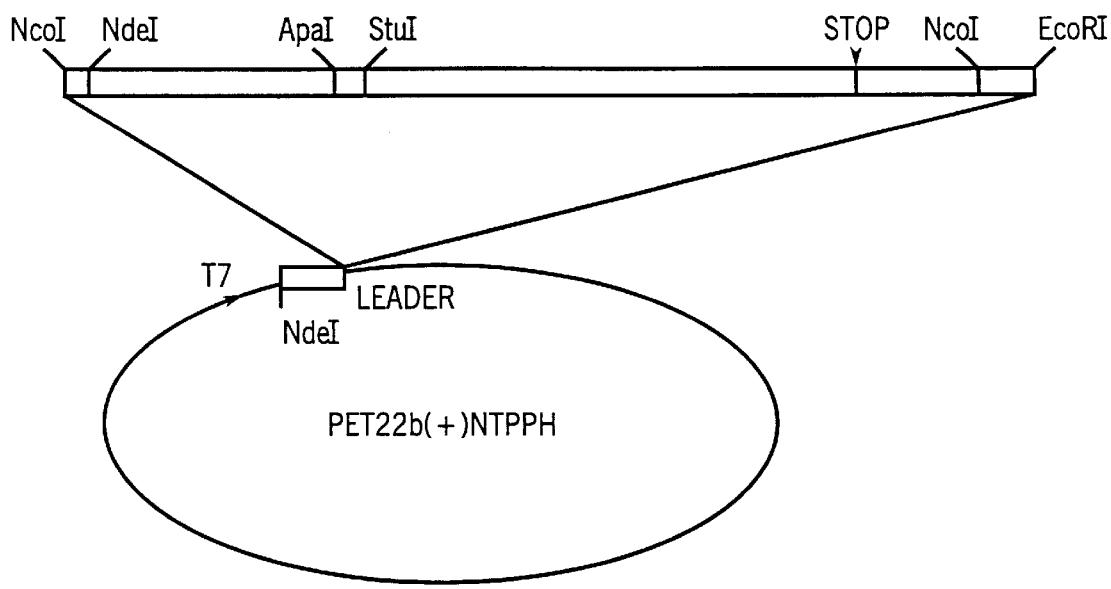
FIG. 3 shows expression vectors PET22b-NTPPH and PET15b-NTPPH.
Figure 3:
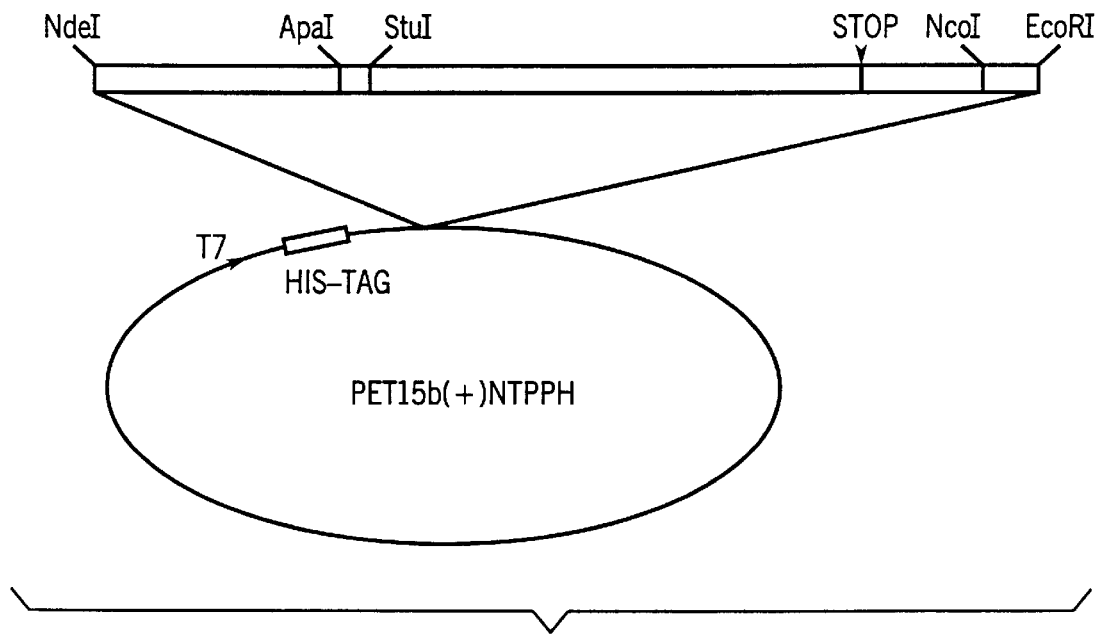

Using cDNA containing 2.5 kbp sequenced insert as a template, PCR fragment from start of N-terminal sequence through StuI site (~600 bp) plus restriction sites with both ends was produced. The PCR fragment was cloned into NcoI/EcoRI cloning site in PET22b vector. The plasmid DNA containing PCR fragment was isolated and digested with StuI and EcoRI. The latter half of 2.5 kbp insert was digested with StuI and EcoRI, and 1.9 kbp fragment was cloned into the PET22b-PCR vector. The transformed vector containing whole cDNA insert (PET22b-NTPPH) (FIG. 3) was infected to BL21 (E. coli strain for expression). Also, DNA fragment from NdeI to EcoRI of PET22b-NTPPH was cloned into NdeI/EcoRI site of PET15b to construct PET15b-NTPPH (FIG. 3).

9. Expression of 61 kD NTPPHase

Expression was induced another 2 hours by adding IPTG to final 0.075M after 2 hours culture at 30° C.

10. Periplasm fraction from PET22b

NTPPH infected cultured cells were extracted and examined immunoreactivity to affinity purified anti 61 kD synthetic peptide antibody (I. Masuda, et al., supra, 1995) on Western Blot.

11. In Vitro Transcription Translation of PET15b-NTPPH

PET15b vector DNA (without insert) as a control template, PET15b-NTPPH DNA was subjected to in vitro transcription translation system (TNT-Coupled Rabbit Reticulocyte Lysate System, Promega, Madison, Wis.) using $^3$H-Leucine label. The in vitro translated products incorporated $^3$H-Leucine. Reactions were incubated at 30° C. for 90 minutes. The expressed polypeptides of the two vectors were separated under denatured conditions on PAGE, enhanced, dried, then visualized by autoradiography.

RESULTS

1. Nucleotide sequence of porcine chondrocyte 61 kD NTPPH

Figure 2:
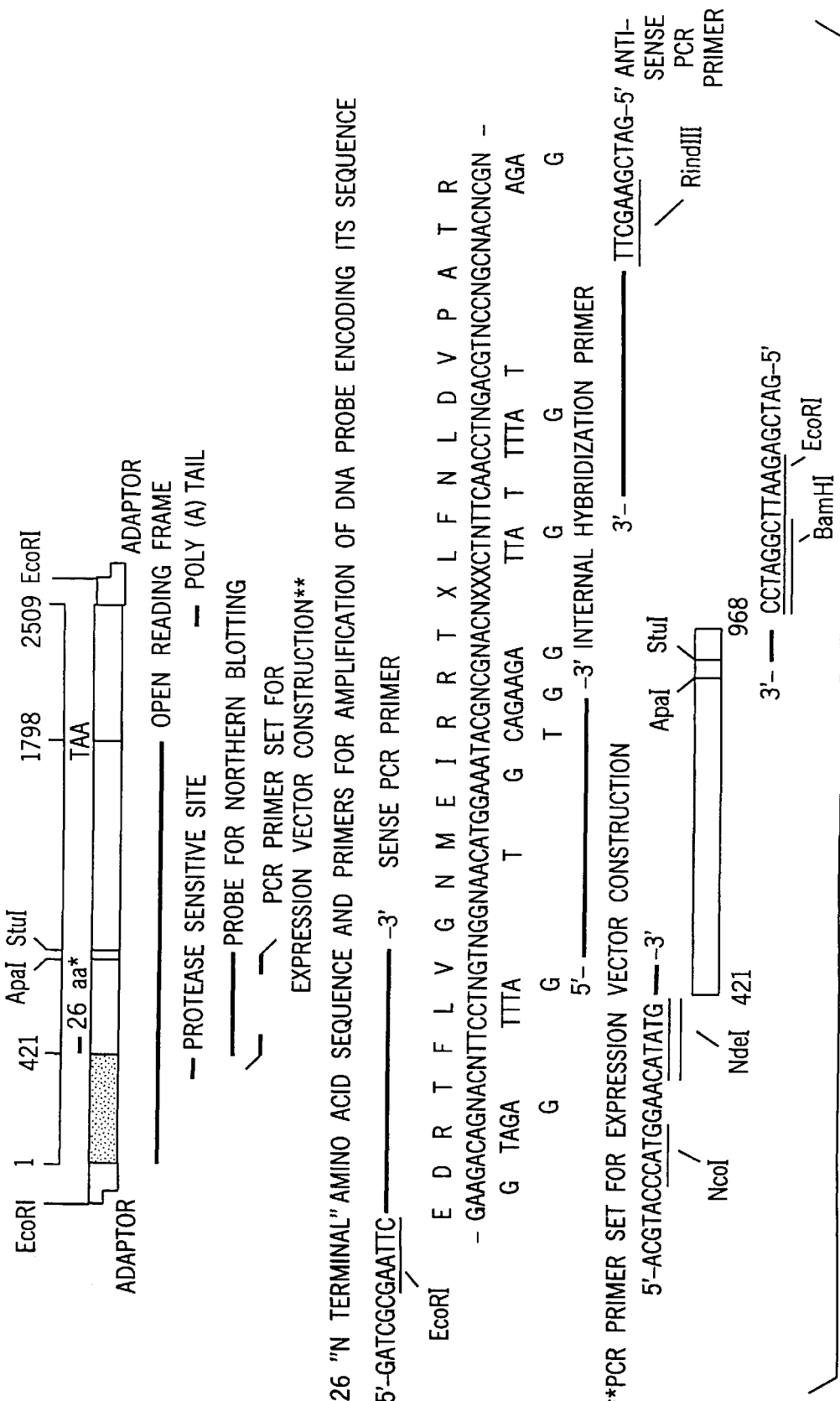
FIG. 2 shows a restriction map of the cloned cDNA encoding 61 kD NTPPH, primer sets for PCR, oligonucleotide for Southern blotting, Northern blotting, and primer sets for construction of expression vector.

The length of the cloned cDNA was 2509 bp (SEQ ID NO:6). Translation of the open reading frame predicts the 61 kD fragment to be a 459 amino acid protein (FIG. 2). The open reading frame continued upstream of the 459 amino acid to 140 amino acid, total 599 partial amino acid sequence (SEQ ID NO:7), which might have given 3'-end of possible 127 kD NTPPH. The downstream of TAA stop codon, there was about 700 bp of untranslated domain including poly(A) tail. There was protease sensitive sequence, RRKRR, upstream of "N terminus" of 61 kD, suggesting a reason we had identified peptide sequence as a "N terminus".

BLAST and FASTA analysis confirmed that this 599 amino acid sequence was unique and did not possess high homology to any known proteins in the non-redundant protein data base. Limited homology (17%) between the 61 kD fragment and several prokaryotic and eukaryotic ATP pyrophosphate-lyase (adenylate cyclase) was detected. However, no distinct functional motifs were detected.

2. Expression of porcine chondrocyte 61 kD NTPPH (a) RNA.

Figure 4:
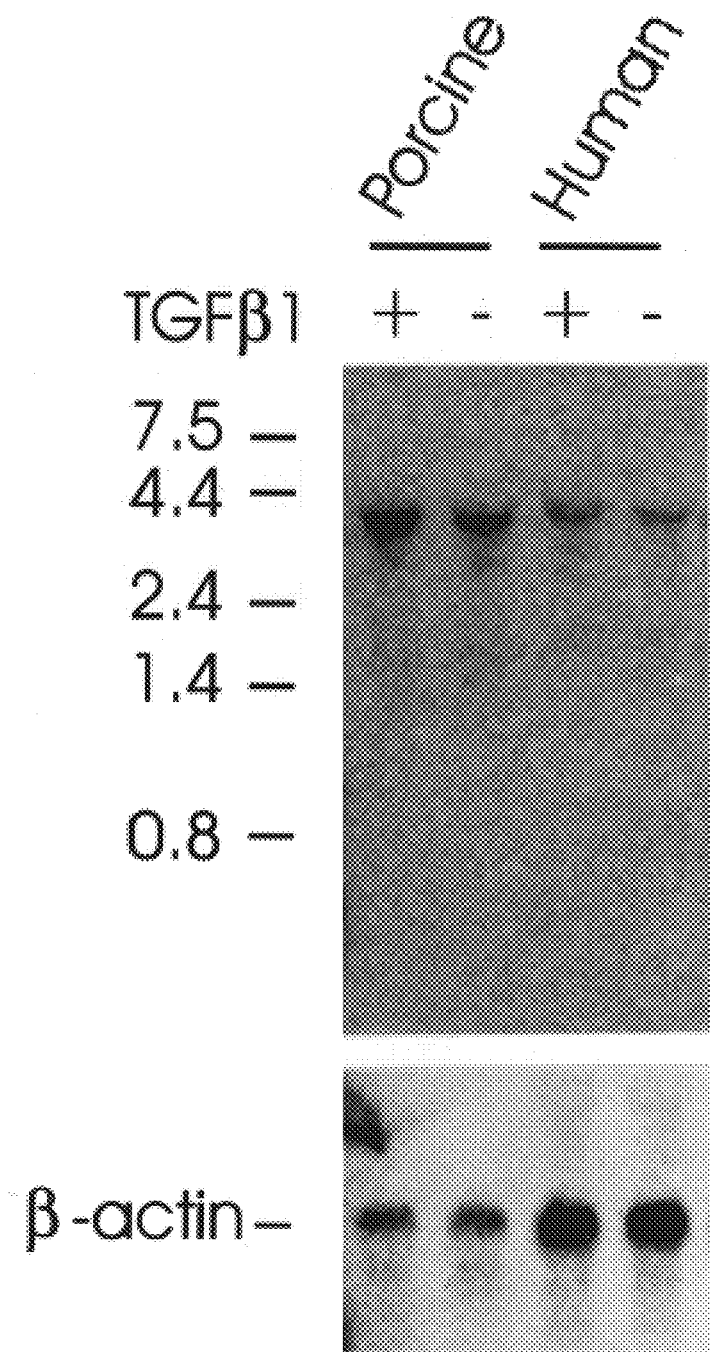
FIG. 4 shows Northern blot analysis of porcine and human chondrocyte RNA using DNA probe encoding porcine chondrocyte 61 kD sequence and chicken β-actin as a control.

Northern blot analysis of porcine and human chondrocyte RNA demonstrated that the DNA encoding the 61 kD NTPPH hybridized to a single 4.3 kbp mRNA transcript (FIG. 4).

(b) Expression in prokaryotic system.

Construction of PET15b-NTPPH and PET22b-NTPPH expression vectors encoding 61 kD NTPPH were successful. However, PET15b-NTPPH has never been able to be transformed in BL21, suggesting this gene may be toxic to the host cells. The chemical induction by IPTG attempting to overexpress 61 kD NTPPH using PET22b-NTPPH failed probably because this gene product causes damage to the host cells, even transiently located in cytoplasm and secreted to periplasm space. We could not maintain transformed PET22b-NTPPH plasmid on plate more than 2 days. Western blot of PET22b-NTPPH periplasm extracted protein showed immunoreactivity to anti 61 kD peptide antibody.

(c) Expression in eukaryotic system in vitro.

Figure 5:
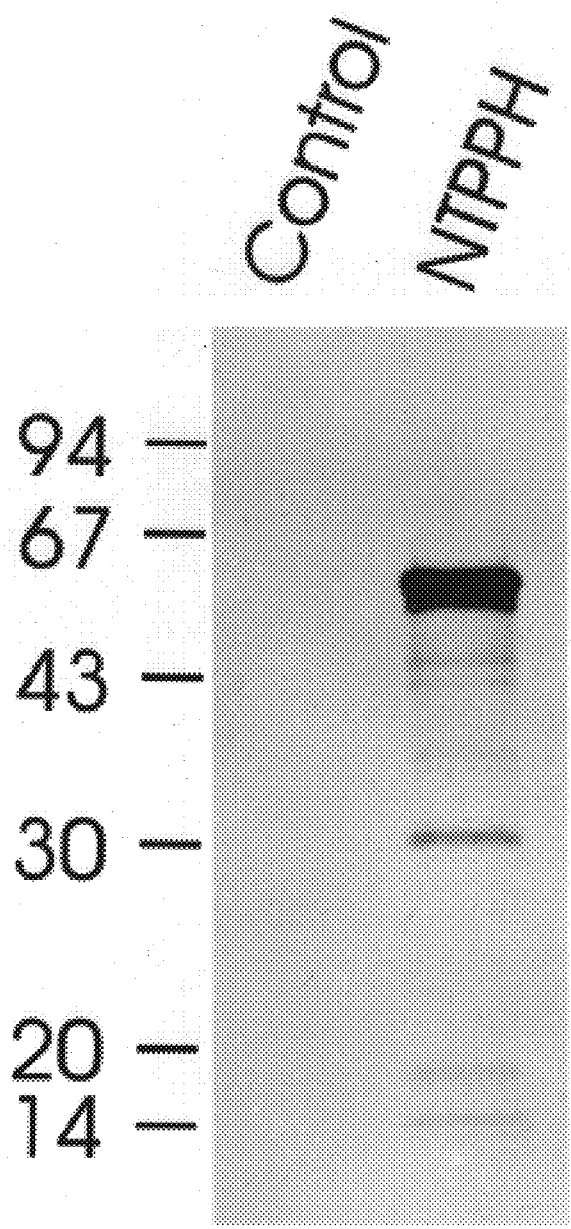
FIG. 5 shows coupled in vitro transcription translation of PET15b-NTPPH DNA with a deletion of leucine and $^3$H-labeled leucine along with PET15b vector DNA without insert as a control.

In vitro transcription translation of PET15b-NTPPH DNA using coupled reticulocyte lysate demonstrated a expected full length of 61 kD band (FIG. 5).

3. Progress in molecular cloning of a porcine chondrocyte NTPPH

We have re-screened the porcine chondrocyte cDNA library and have found other cDNA clones encoding 61/127-kD NTPPH. We have not reached N-terminal of full length cDNA encoding 127-kD NTPPH yet, which is expected ~4 kb. However, re-screening of library and RACE (rapid amplification of cDNA ends) methods enabled us to extend another 300 upstream sequence from SEQ ID NO:6 (SEQ ID NO:8) The confirmation of this extended sequence is still needed.

As described above, a data base homology search for SEQ ID NO:6 did not show any significant homology. The extended sequence (SEQ ID NO:8) was also unique and did not possess a high degree of homology to sequences in the non-redundant protein and nucleotide data bases.

Figure 7:
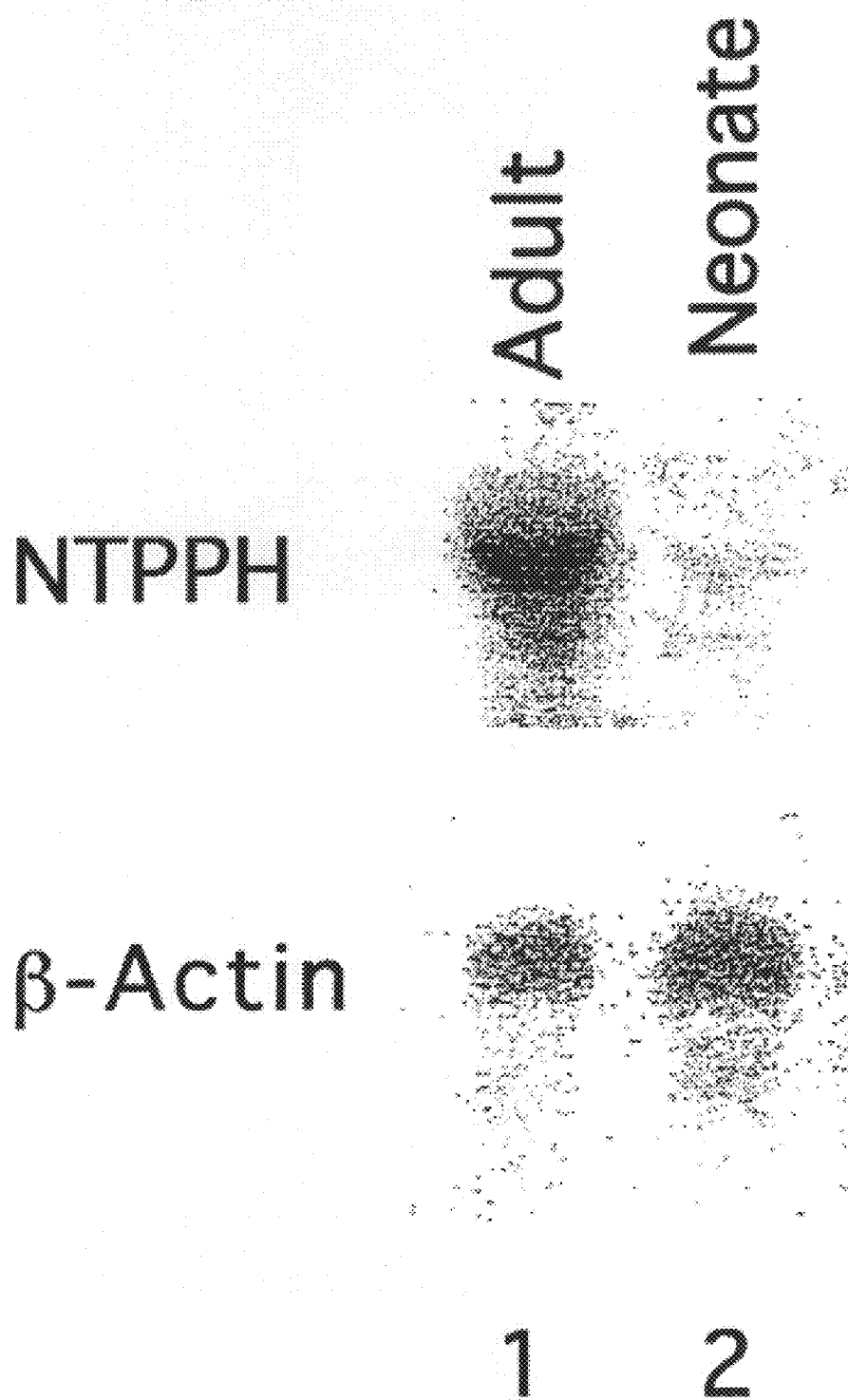
FIG. 7 shows Northern blot analysis of neonatal and adult pig chondrocyte using porcine cDNA probe encoding 61 kD NTPPH sequence.

4. Expression of porcine chondrocyte 61-kD NTPPH mRNA (a) mRNA expression of 61-kD NTPPH in adult and neonatal porcine chondrocytes Northern blot of neonatal and adult pig chondrocyte was performed using porcine cDNA probe encoding 61-kD NTPPH (SEQ ID NO:6, 0.8 kb NcoI-ApaI fragment) (FIG. 7). Each single ~4 kb transcript was detected in both adult and neonatal samples, the expression was much weaker in the neonatal chondrocyte mRNA, suggesting that the expression of NTPPH mRNA may increase with age.

(b) Preliminary studies of Localized expression in porcine articular tissues by immunohistochemistry and in situ hybridization.

Preliminary immunohistochemistry and in situ hybridization (ISH) has been performed in collaboration with Dr. Ken-ichi Iyama, Dept. Surgical Pathology, Kumamoto University School of Medicine, Japan. Adult and neonatal porcine articular cartilage and fibrocartilage (meniscus) were immediately fixed in 4% paraformaldehyde overnight at 4° C., washed 3 times in PBS, dehydrated in a graded series of ethanol washes, and embedded in paraffin. Consecutive sections were cut at 5 mm increments and processed for immunohistochemistry and in situ hybridization.

Immunohistochemical localization of 61-kD NTPPH has been determined using conventional visualization method (ABC method) (1, 2). Sections were pre-digested with hyaluronidase for 20 minutes to avoid epitope masking. Anti N-terminal synthetic peptide of 61-kD NTPPH antibody was used at 1:1000 dilution. Normal rabbit IgG was used as a negative control. In adult cartilage, extracellular matrix through surface to mid-deep zone was reactive, especially the pericellular matrix surrounding the deep zone chondrocytes, but negative in chondrocytes. However, in neonatal cartilage, chondrocytes were reactive in all zones, except in the calcified zone. Extracellular matrix in the superficial zone was reactive but other zones were negative except for the matrix surrounding vessel canals. These differences between adult and neonatal cartilage may reflect the differences in protein secretion of NTPPH with age.

ISH with these same cartilage samples was done using cDNA probe encoding porcine 61-kD NTPPH. Experiments localize the cellular transcriptional distribution of NTPPH. The hybridization procedures that was used have been described elsewhere (3, 4). Briefly, cDNA was labeled with $^{35}$S-thymidine 5'-[α-thio] triphosphate (TTP) (Dupont, Boston, Mass.) by nick-translation. After hybridization, slides were washed at high stringency. The dried tissue sections were dipped into Kodak NTB-2 emulsion and exposed for 3–7 days at 4° C. The sections were counterstained with hematoxylin for image enhancement. As a negative control, parallel sections were also digested before hybridization with 2 mg/ml of RNase for 1 hour at RT. As we found it in Northern blot, mRNA expression in neonatal cartilage or fibrocartilage was clearly weaker and appeared to be under detectable sensitivity. Adult chondrocytes showed strong mRNA expression throughout mid to deeper zones except weak in superficial zone. Signals disappear under the "tide mark".

The summary of immunohistochemistry/ISH results is shown in Table 1.

TABLE 1

Summary of immunostain (α-SNTP) & in situ hybridization (cDNA)

| | Matrix Protein | Chondrocyte Protein | mRNA |
|---|---|---|---|
| Adult Articular Cartilage | | | |
| Superficial (tangenital) layer | + | − | + |
| Middle (transitional) layer | ++ | − | ++ |
| Deep (radial) layer | + (pericellular matrix) | + | +++ |
| Calcified layer | − | − | − |
| Young Articular Cartilage | | | |
| Superficial (tangenital) layer | +− | + | − |
| Middle (transitional) layer | − | + | − |
| Deep (radial) layer | − | ++ | − |
| Calcified layer | − | − | − |
| Adult Meniscus | | | |
| Superficial layer | +++ | +− | + |
| Deep layer | ++ | − | +++ |
| Young Meniscus | | | |
| Superficial layer | − | − | − |
| Deep layer | + | + | − |

5. Progress in cloning of the human homologue of the 127-kD NTPPH from a human chondrocyte cDNA library.

Figure 8:
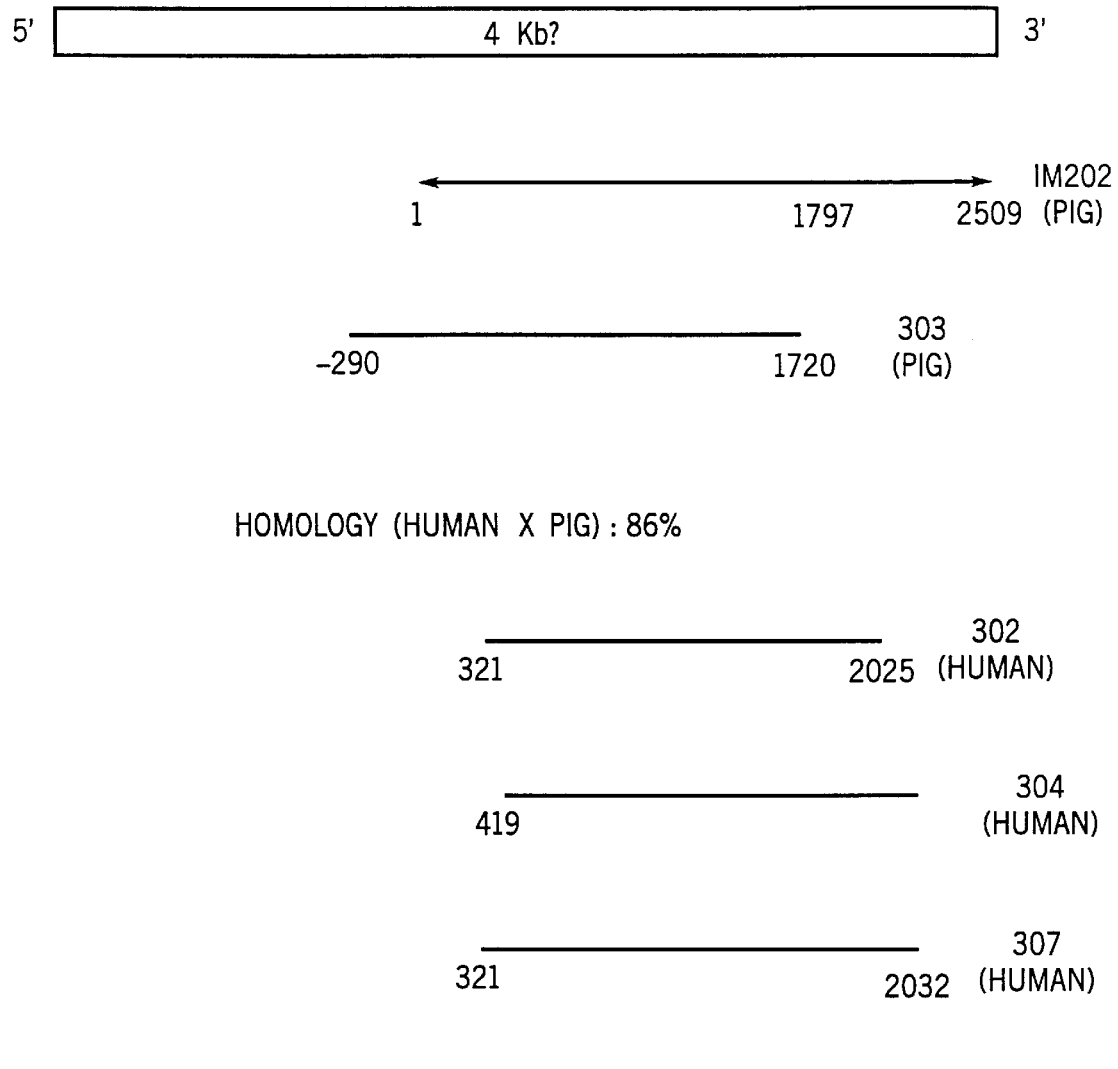
FIG. 8 is a schematic of three human NTPPH cDNA clones.
Figure 9:
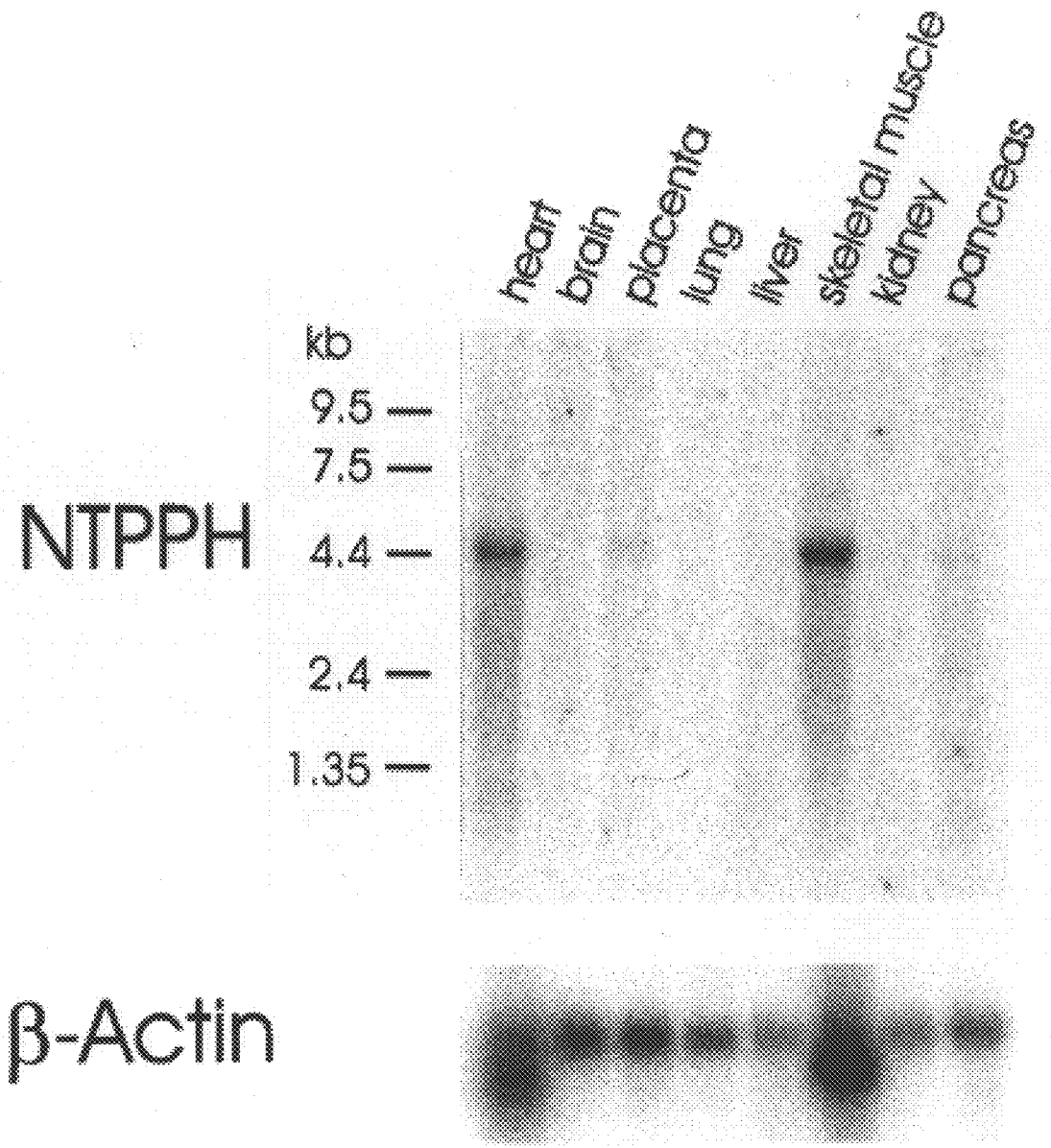
FIG. 9 shows Northern blot analysis of various human tissues with human NTPPH cDNA probe.

We have constructed a human osteoarthritic chondrocyte cDNA library and screened the library with the porcine 61-kD cDNA probe to clone the human homologue. We have three human cDNA clones (IM302, 304, 307) identified to posses 86% homology to porcine cDNA sequence. See FIG. 8. We are currently confirming their sequence, and also getting full length of human cDNA encoding the 127-kD NTPPH using RACE procedure.

(a) Construction of human chondrocyte cDNA library.

A human chondrocyte cDNA library has been constructed using the same methods as described above for the porcine library. The most critical component for the generation of an effective cDNA library is a source of high quality chondrocyte RNA. Human articular cartilage is a reliable source for primary cultures of chondrocytes, which produce a stable mRNA which hybridizes to the cDNA encoding porcine NTPPH. See FIG. 4. Cartilage was obtained from patients with osteoarthritic knees or hips during joint replacement surgery. Cartilage pieces were washed in PBS, digested with trypsin and collagenase, and the released chondrocytes were plated as a high density monolayer. At near confluence, chondrocytes were harvested and total RNA extracted. Since the amount of cartilage was limited, total RNA from a dozen cartilage preparations was pooled to reach the desired 1 mg of total RNA needed to construct the library. Total RNA were subjected to two rounds of oligo(dT) cellulose column chromatography to select for poly(A$^+$) RNA. The library was generated, using the SUPERSCRIPT Choice system (GibcoBRL, Gaithersburg, Md.) to synthesize cDNA from the poly(A$^+$) RNA. A mix of oligo(dT$_{12-18}$) and random hexamer oligonucleotides was used to prime the first strand of cDNA synthesis. This allowed a higher probability of generating cDNAs containing both 5' and 3' ends of the mRNA. EcoRI adapters were added to both ends of cDNA, which were then phosphorylated. The cDNA was ligated into dephosphorylated EcoRI lambda ZAPII phage arms and packaged into phage, using Gigapack Gold (Stratagene, La Jolla, Calif.). Titers of unamplified and amplified library were $1.2 \times 10^6$ and $1.0 \times 10^{10}$ pfu/ml, respectively. The average length of cDNA inserts was 1.3 kb.

(b) Cloning of the human homologue of the 127-kD NTPPH from a human chondrocyte cDNA library.

Since the DNA probe encoding porcine NTPPH hybridized with human chondrocyte transcript, we initially screened the human chondrocyte cDNA library with a probe encoding an internal component of the porcine NTPPH cDNA. Initial screening of 300,000 phage identified 9 strong positive and 15 relatively weak positive plaques at a moderate stringency (0.5×SSC, 55° C.), which hybridized with cDNA encoding porcine NTPPH (nucleotide #41-922 in SEQ ID NO:6).

We isolated and confirmed the positives in subsequent screening rounds. The phagemid containing the cDNA insert was excised by co-infection with helper phage into the SOLR host cell. Phagemid DNA was digested with EcoRI to release the cDNA insert and subcloned into the EcoRI site of M13mp18. The size and restriction map of each independent isolated cDNA was determined and three longest cDNA insert (IM302, 304, and 307), which has hybridized to the porcine NTPPHase probes, as determined by Southern blot, were subjected to DNA sequence analysis. We are currently confirming the sequence of both strands of each cDNA insert by the dideoxy chain-termination method, using fluorescein labeled primers with an ALF DNA Sequencer (Pharmacia Biotech, Piscataway, N.J.). A very preliminary sequence of IM307 is shown in SEQ ID NO:9.

6. mRNA expression in various human tissues

Northern blotting of human multiple tissues was performed. Tissues examined were heart, brain, placenta, liver, lung, skeletal muscle, kidney, pancreas. Pre-loaded human multiple tissue blot was purchased from Clontech, Palo Alto, Calif. Only heart, skeletal muscle showed a transcript hybridized with human cDNA probe (IM307, 0.8 kb EcoRI fragment) encoding 61-kD NTPPH. mRNA expression in muscles were about same size (~4 kb) as in human and porcine chondrocytes that had been described in previous application.

The early immunological study by Western blotting using antibodies to 61-kD and 127-kD NTPPH did not identify the signal in muscle (5). Whether the NTPPH expression in muscle is regulated in post-transcriptional level remains uncertain.

7. Possible valuable application expansion?

We will be able to expand clinical studies to include patients with muscle diseases based upon the recognition of increased NTPPH activity in sera from patients with fibromyalgia and the recognition of expression of 127-kD NTPPH in porcine smooth and skeletal muscle samples in addition to its previously recognized expression in cartilage. The establishment of 127-kD NTPPH specific ELISA to screen patients' sera will be the key of this application. Now, we have sequences of human cDNA clones encoding NTPPH to start making antibodies against recombinant protein or peptides based on this human sequence. We have a large numbers of frozen sera from fibromyalgia patients. Should a correlation exist, this ELISA will be also valuable diagnostic test for fibromyalgia.

8. Background for fibromyalgia (FM)

Our preliminary study of human serum NTPPH activity showed elevated levels in CPPD, OA, and fibromyalgia (FM) (6, 7). It is important to establish the ELISA to test specific 61/127-kD NTPPH levels in human sera and/or synovial fluids as disease correlates. The elevated enzyme levels in FM patients were surprising but interesting because of the fact that no diagnostic test and no significant pathogenetic mechanism in this disease has ever been demonstrated. FM is a chronic musculoskeletal disorder characterized by widespread pain, exquisite tenderness at specific anatomic sites (e.g., tender points), and other clinical manifestations such as fatigue, sleep disturbance, and irritable bowel syndrome. Since the ACR had published the criteria for classifying patients with this disorder in 1990 (8), FM has become a commonly recognized disorder. Its prevalence varies, but has been estimated as 2% in the most recent population-based study (9), and 3–20% in referral-based Rheumatology practice. The pathophysiology of FM is unknown. Both patients and their physician tend to describe the pain of FM as muscular in origin. Bengtsson and colleagues reported reductions in the levels of ATP and phosphocreatine, as well as the appearance of ragged red fibers in the tender areas of the trapezius muscle of patients with FM (10, 11). This may reflect muscle microtrauma rather than a pathogenetic abnormality.

We found that Northern blot analysis of various porcine organ tissues using DNA probe encoding the 61-kD cartilage NTPPHase showed the same size mRNA transcript in skeletal muscle and heart muscle as was seen in articular tissues. Abnormal nucleotide metabolism in muscle may contribute to the pathogenesis of muscle diseases.

DISCUSSION

The cloned porcine chondrocyte 61 kD NTPPH was unique and did not share homology to any known protein. There is an open reading frame translated 599 amino acid (SEQ ID NO:7) (1–1800) and 0.7 kbp untranslated after the stop codon. Only limited homology to ATP pyrophosphate lyase in several prokaryote and eukaryote was identified, suggesting some affinity to ATP, however, there was no indication of functional motifs.

Figure 6:
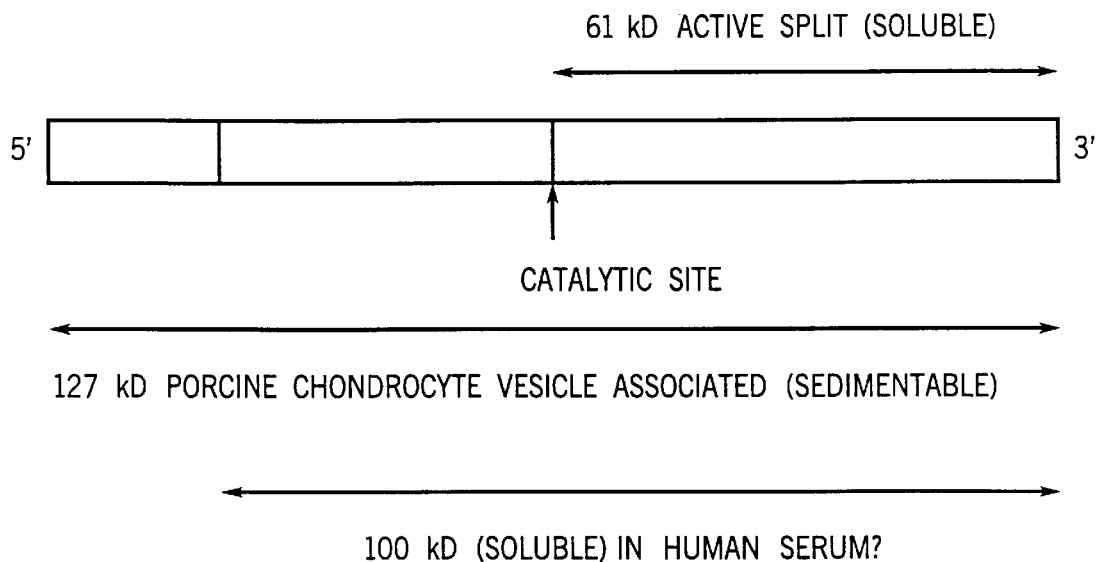
FIG. 6 shows a schematic molecular model of NTPPH native protein.
Figure 6:
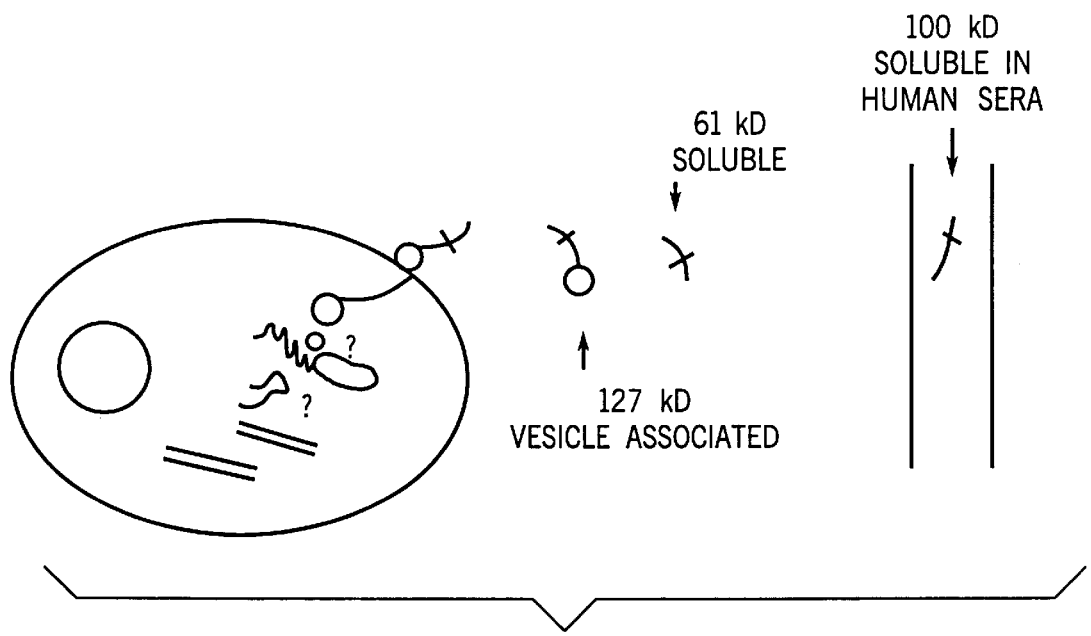

There was protease sensitive sequence that was located upstream of N terminus peptide sequence of 61 kD NTPPH. Absence of starting methionine codon indicated that 61 kD peptide was a cleaved active 3' split of 127 kD NTPPH (FIG. 6). The difficulty to express the 61 kD peptide suggested that this domain was toxic gene to the cell and lacked a stabilizing domain. NTPPH activity certainly should have been tightly regulated inside cell because this enzyme hydrolyzes ATP which has been made inside cell as energy source. NTPPH has been originally identified as an ectoenzyme, which is active outside cells (L. Ryan, et al., 27 *Arthritis Rheum.* 404–409 (1984); A. Caswell and R. Russell, 847 *Biochem. Biophys. Acta.* 40–47 (1985)). 61 kD NTPPH had been purified as an enzymatically active, soluble peptide derived from 127 kD sedimentable form NTPPH in porcine articular cartilage organ culture conditioned media (I. Masuda, et al., supra, 1995). The 127 kD NTPPH was strongly associated with chondrocyte vesicles (I. Masuda, et al., supra, 1995). The 127 kD NTPPH appeared to undergo proteolytic degradation in protease rich inflammatory joint fluid (I. Masuda, et al., supra, 1995). Taken together, we hypothesized that NTPPH was an inactive proenzyme in cytoplasm, then was cleaved out from chondrocyte membrane as vesicle associated 127 kD NTPPH and further cleaved as soluble, and enzymatically active 61 kD NTPPH.

Cloning Human NTPPH Gene

A radiolabelled cDNA for the 61 kD NTPPH can be prepared using standard procedures for cDNA purification. Cells or tissue slices will be fixed on a glass slide, exposed to the cDNA, and hybridized to native mRNA within the cells or tissues. After washing to remove unhybridized cDNA, the tissues or cells will be subjected to autoradiographic preparation and the site and approximate quantity of mRNA can then be visually analyzed.

Analysis of NTPPHase in Serum

Inorganic pyrophosphate ($PP_i$) is elaborated by hyaline cartilage, fibrocartilage, ligamentous and tendinous tissue (A. Rosenthal, et al., 36 *Arthritis Rheum.* 539–542 (1993)). Extracellular $PP_i$ is important in the genesis of calcium pyrophosphate dihydrate crystal deposition (L. Ryan and D. McCarty, supra, 1993). Quantitative studies of $PP_i$ production by human cartilage in organ culture, of intrasynovial $PP_i$ pool size and turnover rate in human knee joints of ATP hydrolysis in cell-free human synovial fluid are most consistent with the hypothesis that the bulk of $PP_i$ production occurs via the breakdown of extracellular ATP by ectonucleotide pyrophosphohydrolase (NTTPPHase) activity (L. Ryan and D. McCarty, *Ann. Rheum. Dis.*).

There is evidence for three ecto-NTPPHases. A 127 kD ultrasedimentable vesicle-associated enzyme and its active degradation products first found in porcine articular cartilage organ culture conditioned medium (I. Masuda, et al., supra, 1995), are also present in synovial fluid from normal persons and patients with arthritis (I. Masuda, et al., supra, 1995). This enzyme was found only in articular tissues (A. Cardenal, et al., supra, 1996). Another NTPPHase, a 115 kD protein found originally in a plasmacytoma and termed PC-1, is a plasma membrane ectoenzyme found in many cell types (A. Harahap and J. Goding, supra, 1988). It is highly expressed in both chondrocytes and bone cells (R. Huang, et al., 94 *J. Clin. Invest.* 560–567 (1994)). Soluble PC-1 has been described (S. Belli, et al., 217 *Eur. J. Biochem.* 421–428 (1993)). This enzyme also has been identified in human synovial fluid (I. Masuda, et al., supra, 1995; R. Huang, et al., supra, 1994). A third 58 kD NTPPHase, has been identified by immunoprecipitation (W. Ono, et al., 38 *Arthritis Rheum.* S244 (1995)). Like PC-1, it is present in synovial fluids and is expressed in many cell types.

Judging by the frequent finding of smaller reactive fragments in Western blot, all three enzymes undergo proteolysis in synovial fluid. Intact 115 kD PC-1 was found in only 2 of 29 human synovial fluids, although fragments of smaller molecular mass were often found. Of the three enzymes, PC-1 appears most susceptible to proteolysis. The 127 kD vesicle-associated enzyme was extensively degraded only in fluid from inflamed joints and was found in all three normal joint fluids.

Approximately 60 to 80% of serum NTPPHase activity from 9 consecutive arthritis patients and from two normal subjects was eluted as a single peak on dye chromatography and reacted only with antibodies to the 127 kD enzyme (A. Cardenal, et al., supra, 1996). No other active NTPPHase was found in any of these sera. The reactant in all sera was a soluble ~100 kD protein with kinetic characteristics identical to those of the sedimentable 127 kD enzyme (A. Cardenal, et al., supra, 1996). Serum and plasma prepared form the same blood specimen had virtually identical NTPPHase activity (W. Park, et al.,*J. Rheumatol.* (in press)). The apparent tissue specificity of the 127 kD NTPPHase coupled with the constant finding of a soluble product of this enzyme in serum suggested that measurement might serve as a marker of articular tissue metabolism.

Sera were prepared from 15 normal healthy men, 31 normal healthy women and 157 patients with various rheumatic diseases. For analysis of results, patients were grouped according to their clinical diagnosis. Seropositive rheumatoid arthritis (RA) patients with active disease (n=16) were analyzed separately from those in remission (n=24).

Serum NTPPHase levels were easily measured reproducibly (coefficient of variation 8%). Activity was present in all sera studied, and reproducible in specimens prepared from blood taken on different occasions (coefficient of variation also 8%). NTPPHase levels were elevated significantly in patients with symptomatic degenerative arthritis whether or not they had CPPD crystal deposition. Neither the osteoarthritis or CPPD deposition group were different from a small group of women with fibromyalgia, but the values in fibromyalgia were significantly greater than those found in normal women or patients with seropositive rheumatoid arthritis. This surprising finding obviously needs further study.

Previous studies have shown that 127 kD ectoNTPPHase is expressed only in extracellular vesicles produced by hyaline, fibrous and elastic cartilage, ligamentous and tendinous tissues (A. Cardenal, et al., supra, 1996) and by synovial cells (I. Masuda, et al., supra, 1995). A ~100 kD soluble moiety of 127 kD NTPPHase was subsequently identified in serum from normal subjects and patients with various types of arthritis (A. Cardenal, et al., supra, 1996). We speculate that serum soluble NTPPHase was derived from partial proteolysis of the parent enzyme molecule, gaining access to the bloodstream by lymphatic clearance from synovial and other connective tissue spaces. The fall in serum values in two women after total knee arthroplasty is consistent with this hypothesis. A systematic study of serum NTPPHase activity before and after joint replacement might be of interest. The low NTPPHase level in the single patient with seropositive rheumatoid arthritis, the only patient in this series who was wheelchair bound, could have been due to his relative immobility with decreased muscular activity leading to decreased lymphatic drainage and/or to increased proteolysis of NTPPHase in actively inflamed joints (I. Masuda, et al., supra, 1995). A study of relatively immobile patients such as those with spinal cord injury might shed further light on these conjectures.

A study of the effect of rest and exercise on serum NTPPHase levels would also be useful, as would a study of physical modalities, such as prolonged immersion in water at various temperatures. The only man in the osteoarthritis/ spondylosis group with an strikingly elevated NTPPHase value was taking cyclosporine for a heart transplant. A systematic study of the effect of this drug on serum NTPPHase values would also be of interest.

The apparent uniqueness of expression of ecto 127 kD NTPPHase in connective tissue, its ubiquitous presence in normal and pathologic sera, the absence of other active ectoNTPPHases in serum and the ease of the assay all suggest that quantification of this enzyme activity might prove useful in the study of patients with certain diseases or syndromes involving connective tissue. Further studies of serum NTPPHase activity levels with careful clinical correlation is needed to fully assess its significance and possible usefulness.

One such study would utilize the cDNA of the present invention to generate a 61 kD NTPPH of sufficient purity to serve as a standard for immunologically based assays of serum and joint fluid determinations of the parent 127 kD NTPPH and its breakdown products. These determinations may be useful in predicting CPPD crystal formation. Since this enzyme is restricted to articular tissues, its detection in elevated quantities in joint fluid or blood would imply joint tissue damage. Thus, this assay would ignore interference from the other types of ecto-NTPPHases found in sera.

Assays of Biologic Fluids

The cDNA of the present invention can be used to generate 61 kD NTPPH of sufficient purity to serve as a standard for assays of biologic fluids. cDNA for the 61 kD NTPPH will be expressed in E. coli or another suitable expression system. Expressed protein will be affinity purified or purified according to the methods set forth in Masuda, et al. 95 *J. Clin. Invest.* 699–705 (1995). Diluted protein can then be used for determination of standard curves in the quantitation of NTPPH in biologic fluids using standard ELISA techniques.

Literature Cited

1. Ishikawa, K., Masuda, I., Ohira, T., Yokoyama, M.: A histologic study of calcium pyrophosphate dihydrate crystal-deposition disease. *J. Bone and Joint Surg.* 71-A:875–886, 1989.
2. Masuda, I., Ishikawa, K., Usuku, G.: A histologic and immunohistochemical study of calcium pyrophosphate dihydrate crystal deposition disease. *Clin. Orthop.* 263:272–287, 1991.
3. Hayashi, M., Ninomiya, Y., Parsons, J., Hayashi, K., Olsen, B. R., Trelstad, R. L.: Differential localization of mRNAs of collagen type I and II in chick fibroblasts, chondrocytes, and corneal cells by in situ hybridization using cDNA probes. *J. Cell Biol.* 102:2302–2309, 1986.
4. Iyama, K., Ninomiya, Y., Olsen, B. R., Lisenmayer, T. F., Trelstad, R. L., Hayashi, M.: Spatiotemporal pattern of type X collagen gene expression and collagen deposition in embryonic chick vertebrae undergoing endochondral ossification. *Anat. Rec.* 229:462–472, 1991.
5. Cardenal, A., Masuda, I., Haas, A. L., McCarty, D. J.: Specificity of a porcine 127 kD nucleotide pyrophosphohydrolase for articular tissues. *Arthritis Rheum.* 39:245–251, 1996.
6. Cardenal, A., Masuda, I., Haas, A. L., Ono, W., McCarty, D. J.: Identification of a nucleotide pyrophosphohydrolase from articular tissues in human serum. *Arthritis Rheum.* 39:252–256, 1996.
7. Cardenal, A., Masuda, I., Ono, W., Haas, A. L., Ryan, L. M., Csuka, M. E., Trotter, D., McCarty, D. J.: Serum nucleoside triphosphate pyrophosphohydrolase (NTPPHase) activity: elevated levels in osteoarthritis, calcium pyrophosphate crystal deposition disease and fibromyalgia. *Arthritis Rheum.* 39:S83, 1996. (Abstract)
8. Wolfe, F., Smythe, H. A., Yunus, M. B., et al.: The American College of Rheumatology 1990 criteria for the classification of fibromyalgia. Report of the multicenter criteria committee. *Arthritis Rheum.* 33:160–172, 1990.
9. Wolfe, F., Ross, K., Anderson, J., Russell, I. J., Hebert, L.: The prevalence and characteristics of fibromyalgia in the general population. *Arthritis Rheum.* 38:19–28, 1995.
10. Bengtsson, A., Henriksson, K. G., Larsson, J.: Muscle biopsy in primary fibromyalgia: light-microscopical and histochemical findings. *Scand. J. Rheumatol.* 15:1–6, 1986.
11. Bengtsson, A., Henriksson, K. G., Larsson, J.: Reduced high-energy phosphate levels in the painful muscles of patients with primary fibromyalgia. *Arthritis Rheum.* 29:817–821, 1986.

We claim:

1. An isolated RNA construct encoding for nucleotide pyrophosphohydrolase that can hybridize with an isolated DNA sequence of SEQ ID NO:6 when the RNA construct and the DNA construct are subjected to Northern blot analysis.

2. The isolated RNA construct of claim 1, wherein the RNA is isolated human RNA.

3. An isolated DNA sequence of SEQ ID NO:6 encoding a soluble form of nucleotide pyrophosphohydrolase (NTPPH).

* * * * *

UNITED STATES PATENT AND TRADEMARK OFFICE
CERTIFICATE OF CORRECTION

PATENT NO. : 5,986,080 Page 1 of 1
DATED : November 16, 1999
INVENTOR(S) : Masuda et al.

It is certified that error appears in the above-identified patent and that said Letters Patent is hereby corrected as shown below:

<u>Column 1,</u>
Line 9, insert the following:
-- STATEMENT REGARDING FEDERALLY SPONSORED RESEARCH OR DEVELOPMENT The U.S. government has a paid-up license in this invention and the right in limited circumstances to require the patent owner to license others on reasonable terms as provided for by the terms of contract No. R01 AR 38656 awarded by the National Institute of Arthritis and Musculoskeletal and Skin Diseases of the National Institutes of Health. --

Signed and Sealed this

Seventh Day of October, 2003

JAMES E. ROGAN
*Director of the United States Patent and Trademark Office*